United States Patent
Reddy et al.

(10) Patent No.: US 11,766,571 B2
(45) Date of Patent: Sep. 26, 2023

(54) RETENTION MECHANISM FOR AN IMPLANTABLE LEAD

(71) Applicant: CARDIAC PACEMAKERS, INC., St. Paul, MN (US)

(72) Inventors: G. Shantanu Reddy, Minneapolis, MN (US); Benjamin Michael Nitti, Scandia, MN (US); Bryan Peter Nelson, Woodbury, MN (US); Christopher Alan Fuhs, Roseville, MN (US); Andrew L. De Kock, Ham Lake, MN (US); Peter Hall, Andover, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 2 days.

(21) Appl. No.: 17/527,703

(22) Filed: Nov. 16, 2021

(65) Prior Publication Data
US 2022/0072317 A1   Mar. 10, 2022

Related U.S. Application Data

(63) Continuation of application No. 16/519,679, filed on Jul. 23, 2019, now Pat. No. 11,202,915.
(Continued)

(51) Int. Cl.
*A61N 1/05* (2006.01)
*A61N 1/375* (2006.01)

(52) U.S. Cl.
CPC ......... *A61N 1/3752* (2013.01); *A61N 1/0504* (2013.01); *A61N 1/057* (2013.01);
(Continued)

(58) Field of Classification Search
CPC .. A61N 1/3752; A61N 1/0504; A61N 1/0563; A61N 1/057; A61N 2001/058;
(Continued)

(56) References Cited

U.S. PATENT DOCUMENTS

| 4,716,888 A | 1/1988 | Wesner |
| 4,913,164 A * | 4/1990 | Greene ................. A61N 1/057 |
| | | 607/126 |

(Continued)

FOREIGN PATENT DOCUMENTS

| EP | 0085967 A1 | 8/1983 |
| WO | 2012151356 A1 | 11/2012 |

OTHER PUBLICATIONS

International Search Report and Written Opinion dated Oct. 29, 2019 for International Application No. PCT/US2019/042995.
(Continued)

*Primary Examiner* — Carl H Layno
*Assistant Examiner* — Anh-Khoa N Dinh
(74) *Attorney, Agent, or Firm* — Seager, Tufte & Wickhem LLP

(57) ABSTRACT

A retention device for use with an implantable medical device (IMD) may comprise an elongate body including a configured to receive the lead of the IMD. The retention device may also include securing mechanisms coupled to the elongate body and configured to push against tissue of a patient. The securing mechanisms may also include linking elements coupled to the elongate body and a portion of the securing mechanisms.

18 Claims, 34 Drawing Sheets

Related U.S. Application Data

(60) Provisional application No. 62/702,092, filed on Jul. 23, 2018.

(52) U.S. Cl.
 CPC ...... *A61N 1/0563* (2013.01); *A61N 2001/058* (2013.01); *A61N 2001/0582* (2013.01)

(58) Field of Classification Search
 CPC .... A61N 2001/0582; A61M 2205/587; A61M 25/00; A61M 25/06; A61M 2025/0293; A61M 2039/0223; A61M 2039/0261; A61M 25/0194; A61M 25/02; A61M 25/0133; A61M 29/00; A61B 17/3423; A61B 17/3468; A61B 2017/3427; A61B 2017/3482; A61B 2017/3488; A61B 2017/3492; A61B 5/0538; A61B 5/287; A61B 5/4836; A61B 5/6851; A61B 5/686; A61B 5/6876

See application file for complete search history.

(56) References Cited

U.S. PATENT DOCUMENTS

| | | | |
|---|---|---|---|
| 4,957,118 A * | 9/1990 | Erlebacher | A61N 1/057 607/128 |
| 6,647,292 B1 | 11/2003 | Bardy et al. | |
| 6,721,597 B1 | 4/2004 | Bardy et al. | |
| 7,149,575 B2 | 12/2006 | Ostroff et al. | |
| 7,194,302 B2 | 3/2007 | Bardy et al. | |
| 7,493,175 B2 | 2/2009 | Cates et al. | |
| 7,655,014 B2 | 2/2010 | Ko et al. | |
| 8,019,443 B2 | 9/2011 | Schleicher et al. | |
| 8,244,377 B1 | 8/2012 | Pianca et al. | |
| 8,285,397 B2 | 10/2012 | Grandhe | |
| 8,332,043 B1 | 12/2012 | Jaax et al. | |
| 8,676,352 B2 | 3/2014 | Geistert et al. | |
| 9,610,435 B2 | 4/2017 | Schleicher et al. | |
| 9,981,121 B2 | 5/2018 | Seifert et al. | |
| 10,617,402 B2 | 4/2020 | Reddy et al. | |
| 2002/0111664 A1 * | 8/2002 | Bartig | A61N 1/0563 607/122 |
| 2004/0230279 A1 | 11/2004 | Cates et al. | |
| 2004/0230282 A1 | 11/2004 | Cates et al. | |
| 2007/0255295 A1 | 11/2007 | Starkebaum et al. | |
| 2008/0208247 A1 | 8/2008 | Rutten et al. | |
| 2009/0125059 A1 | 5/2009 | Verzal et al. | |
| 2009/0210043 A1 | 8/2009 | Reddy | |
| 2010/0131036 A1 | 5/2010 | Geistert et al. | |
| 2010/0256696 A1 * | 10/2010 | Schleicher | A61N 1/05 607/116 |
| 2011/0054580 A1 | 3/2011 | Desai et al. | |
| 2011/0054581 A1 | 3/2011 | Desai et al. | |
| 2013/0131767 A1 | 5/2013 | Desai et al. | |
| 2014/0144580 A1 | 5/2014 | Desai et al. | |
| 2014/0194963 A1 | 7/2014 | Desai et al. | |
| 2014/0330248 A1 | 11/2014 | Thompson-Nauman et al. | |
| 2014/0330327 A1 | 11/2014 | Thompson-Nauman et al. | |
| 2015/0133953 A1 * | 5/2015 | Seifert | A61B 17/3468 606/129 |
| 2015/0343199 A1 | 12/2015 | Wechter et al. | |
| 2015/0352352 A1 | 12/2015 | Soltis et al. | |
| 2016/0143643 A1 | 5/2016 | Smith et al. | |
| 2016/0339233 A1 | 11/2016 | De Kock et al. | |
| 2017/0020551 A1 | 1/2017 | Reddy et al. | |
| 2017/0021159 A1 | 1/2017 | Reddy et al. | |
| 2017/0095657 A1 | 4/2017 | Reddy et al. | |
| 2017/0319845 A1 | 11/2017 | De Kock et al. | |
| 2017/0319864 A1 | 11/2017 | De Kock et al. | |
| 2018/0036527 A1 | 2/2018 | Reddy et al. | |
| 2018/0036547 A1 | 2/2018 | Reddy | |
| 2018/0078252 A1 | 3/2018 | Sato | |
| 2018/0133458 A1 | 5/2018 | Foster et al. | |
| 2018/0133462 A1 | 5/2018 | Reddy | |
| 2018/0133463 A1 | 5/2018 | Reddy | |
| 2018/0133494 A1 | 5/2018 | Reddy | |
| 2018/0169384 A1 | 6/2018 | Reddy et al. | |
| 2018/0169425 A1 | 6/2018 | Reddy et al. | |
| 2018/0193060 A1 | 7/2018 | Reddy et al. | |
| 2018/0214686 A1 | 8/2018 | De Kock et al. | |
| 2018/0296824 A1 | 10/2018 | De Kock et al. | |
| 2018/0344200 A1 | 12/2018 | Thakur et al. | |
| 2018/0344252 A1 | 12/2018 | An et al. | |
| 2019/0054289 A1 | 2/2019 | Reddy et al. | |
| 2019/0054290 A1 | 2/2019 | De Kock et al. | |
| 2019/0054302 A1 | 2/2019 | Reddy et al. | |
| 2019/0117959 A1 | 4/2019 | Reddy | |
| 2019/0151651 A1 | 5/2019 | Reddy et al. | |

OTHER PUBLICATIONS

Darrat et al; "Single Incision Technique for Placement of Subcutaneous Implantable Cardioverter Defibrillators," http://abstractsonline.com/pp8/, accessed May 14, 2018.

International Search Report and Written Opinion dated Sep. 18, 2019 for International Application No. PCT/US2019/028506.

* cited by examiner

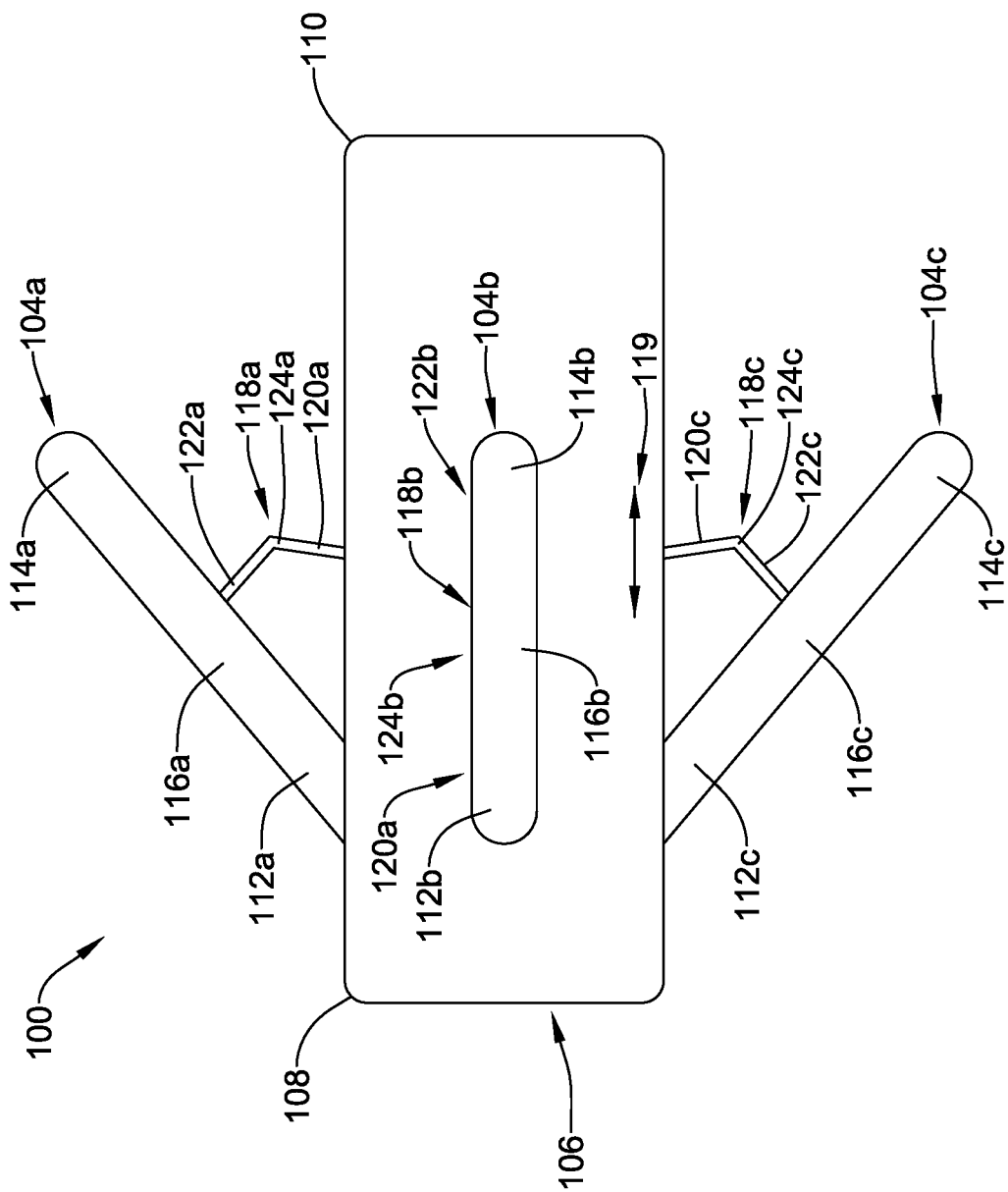

RETENTION MECHANISM FOR AN IMPLANTABLE LEAD

CROSS REFERENCE TO RELATED APPLICATIONS

The present application is a continuation of U.S. patent application Ser. No. 16/519,679, filed Jul. 23, 2019, now U.S. Pat. No. 11,202,915 B2, which claims the benefit of and priority to U.S. Prov. Pat. App. No. 62/702,092, filed Jul. 23, 2018, both titled RETENTION MECHANISM FOR AN IMPLANTABLE LEAD, the disclosures of both of which are incorporated herein by reference.

BACKGROUND

The subcutaneous implantable cardioverter-defibrillator (S-ICD System) from Boston Scientific is implanted, according to the original FDA labeling thereof, with a subcutaneous lead extending from an implanted pulse generator in an axillary pocket, over the ribs to the xiphoid process, and then superiorly along the left side of the sternum. The implant method as originally approved calls for a suture sleeve fixation near the xiphoid. To affix the suture sleeve at this location to the fascia requires looping a suture around the suture sleeve and attachment of the suture to the fascia, through an incision near the xiphoid. Many early implantations used three incisions, one for the pulse generator, one at the xiphoid, and one at a superior location along the sternum, close to but inferior to the manubrium, where the tip of the lead would be placed and secured by suturing to the fascia.

The suturing steps that are used to secure the lead in position relative to the thorax may extend procedure time. It would be advantageous to reduce such suturing steps, not just to reduce procedure time but potentially also to reduce the needed size of incisions, particularly at the xiphoid incision. There is significant interest in reducing procedure time and simplifying the implant procedure by avoiding such suture steps. Moreover, the multiple incisions called for in the S-ICD System implantation procedure raise risks of infection and leave small but visible scars. This has led to interest in simplification of the implant procedure by reducing the number of incisions from 3 to 2, while continuing to ensure the lead is anchored in a desired position.

New and alternative methods and devices for securing a lead, whether for the S-ICD System or other devices, are desired.

OVERVIEW

The present inventors have recognized that a new and useful innovation may include a retention device and method of using a retention device for aiding in the placement of a lead. Such a retention device may be placed on a distal portion of a lead.

A first illustrative and non-limiting example is a retention device for use with an implantable medical device (IMD) that may have a lead. The lead may have a proximal end for coupling to a canister and a distal end. The retention device may include an elongate body that may have a proximal end, a distal end, and a hollow lumen extending from the proximal end to the distal end configured to receive the lead. The retention device may also include one or more securing mechanisms that may have a first end coupled to the elongate body, a second end configured to push against tissue of a patient, and an intermediate portion extending between the first and second ends. The retention device may also include one or more first linking elements that may have a first end coupled to the elongate body and a second end coupled to the intermediate portion of one of the securing mechanisms.

Additionally or alternatively to the first illustrative, non-limiting example, the retention device may have at least two securing mechanisms and further comprise one or more second linking elements, the one or more second linking elements may have a first end coupled to a first one of the securing mechanisms and a second end coupled to a second one of the securing mechanisms.

Additionally or alternatively to any of the above, non-limiting examples, the at least two securing mechanisms may comprise a plurality of securing mechanisms circumferentially spaced about the elongate body and the second linking elements link together adjacent ones of the securing mechanisms.

Additionally or alternatively to any of the above, non-limiting examples, the first and second linking elements may be configured to prevent prolapse of the securing mechanisms.

Additionally or alternatively to any of the above, non-limiting examples, the first linking elements may be configured to limit the extension of the second end of the one or more securing mechanisms away from the elongate body.

Additionally or alternatively to any of the above, non-limiting examples, the one or more securing mechanisms may be configured for movement between a delivery configuration, in which the securing mechanisms may be collapsed toward the elongate body, and a deployed configuration in which the linking element stops the one or more securing mechanism from extending beyond a predefined angle relative to the elongate body.

Additionally or alternatively to any of the above, non-limiting examples, the predefined angle is in the range of about 10 to about 60 degrees.

A second illustrative and non-limiting example is a retention device for use with an implantable medical device (IMD) that may have a lead. The lead may have a proximal end for coupling to a canister and a distal end. The retention device may include an elongate body that may have a proximal end, a distal end, and defining a hollow lumen extending from the proximal end to the distal end configured to receive the lead. The retention device may also include two or more securing mechanisms and each may have a first end coupled to the elongate body, a second end configured to push against tissue of a patient, and an intermediate portion extending between the first and second ends. The retention device may also include one or more first linking elements that may have a first end coupled to a first one of the securing mechanisms and a second end coupled to a second one of the securing mechanisms.

Additionally or alternatively to any of the above, non-limiting examples, the two or more securing mechanisms may comprise a plurality of securing mechanisms circumferentially spaced about the elongate body and second linking elements link together adjacent ones of the securing mechanisms.

Additionally or alternatively to any of the above, non-limiting examples, the flexible material may comprise a polymeric material.

Additionally or alternatively to any of the above, non-limiting examples, the flexible material may comprise silicone.

A third illustrative and non-limiting example is a retention device for use with an implantable medical device (IMD).

The retention device may include an elongate body having a proximal end, a distal end, a hollow lumen extending from the proximal end to the distal end and may be configured to receive a lead of the IMD. The retention device may further include one or more securing mechanisms may have a first end that may be configured to bend such that a portion of the one or more securing mechanisms extends to a predefined angle relative to the elongate body, wherein the one or more securing mechanisms may include a second end that may be configured to extend to the predefined angle and push against tissue of a patient, and wherein the elongate body may be generally tubular with the securing mechanisms formed from a cut portion of the tube.

Additionally or alternatively to any of the above, non-limiting examples, the cut portion of the tube may be located between the proximal and distal ends thereof.

Additionally or alternatively to any of the above, non-limiting examples, the cut portion of the tube may be located at an end thereof.

Additionally or alternatively to any of the above, non-limiting examples, the one or more securing mechanisms may comprise nitinol, the nitinol may be adapted to assume a shape above the transition temperature thereof that facilitates anchoring in tissue.

A fourth illustrative and non-limiting example is an implantable medical device system that may comprise an implantable pulse generator that may comprise a canister housing operational circuitry adapted to generate a therapy output, a lead adapted for coupling to the implantable pulse generator and adapted to deliver the therapy output from the implantable pulse generator, and a retention device as in any of the preceding examples, wherein the lead may be sized and shaped to be received in the hollow lumen of the retention device.

A fifth illustrative and non-limiting example is a method of implanting an implantable lead that may have a first end for coupling to an implantable medical device and a second end for implantation at a target site in the patient, with a lead body extending therebetween. The method may comprise the use of a retention device as in any of the above examples. The method may include inserting the implantable lead into the patient with the retention device placed on the lead at a desired location thereon and with a sheath disposed about at least a portion of the lead and compressing the one or more securing mechanisms of the retention device in a delivery configuration. The method may also include at least partly withdrawing the sheath such that the one or more securing mechanisms extend to a deployed configuration to anchor the implantable lead to tissue of the patient.

Additionally or alternatively to the fifth illustrative, non-limiting example, the step of inserting the implantable lead may be performed by making a first incision and a second incision, making a first tunnel between the first and second incisions, making a second tunnel from the second incision to an end location, and passing at least the second end of the implantable lead through the second incision to the end location, wherein the step of inserting the implantable lead may be performed such that the retention device may be accessible near the second incision, and the method may further comprise positioning the retention device near a xiphoid of the patient and partly withdrawing the sheath allowing the one or more securing mechanisms to extend to the deployed configuration and push against tissue of the patient near the second incision to secure the lead in a selected position.

A sixth illustrative and non-limiting example is a retention device for use with an implantable medical device (IMD). The retention device may comprise an elongate body having a proximal end, a distal end, a hollow lumen extending from the proximal end to the distal end that may be configured to receive a lead of the IMD. The retention device may further include one or more securing mechanisms that may have a first end that may be configured to bend such that a portion of the one or more securing mechanisms extends to a predefined angle relative to the elongate body.

Additionally or alternatively to any of the above, non-limiting examples, the one or more securing mechanisms may include a second end that may be configured to extend to the predefined angle and push against tissue of a patient.

Additionally or alternatively to any of the above, non-limiting examples, the elongate body may be generally tubular with the securing mechanisms formed from a cut end of the tube.

Additionally or alternatively to any of the above, non-limiting examples, the elongate body may be generally tubular with the securing mechanisms formed from a cut portion of the elongate body located between the proximal and distal ends thereof.

Additionally or alternatively to any of the above, non-limiting examples, the one or more securing mechanisms may further include a second end that may be configured to bend to the predefined angle in an opposite direction as the predefined angle from the bend of the first end, and an intermediate section between the first end and the second end that may be configured to extend away from the elongate body and push against tissue of a patient.

Additionally or alternatively to any of the above, non-limiting examples, the intermediate section may further include a bend.

Additionally or alternatively to any of the above, non-limiting examples, each of the one or more securing mechanisms may be capable of shifting between a delivery configuration and a deployed configuration.

Additionally or alternatively to any of the above, non-limiting examples, in the deployed configuration the first end may be bent and the one or more securing mechanisms may be extended to the predefined angle relative to the elongate body.

Additionally or alternatively to any of the above, non-limiting examples, the predefined angle may be in the range of about 10 to about 60 degrees.

Additionally or alternatively to any of the above, non-limiting examples, the one or more securing mechanisms may comprise a plurality of securing mechanisms circumferentially spaced from one another, with gaps separating the plurality of securing mechanisms.

Additionally or alternatively to any of the above, non-limiting examples, the gaps may be non-constant such that there is a larger distance separating first ends of adjacent securing mechanisms, from the plurality of securing mechanisms, than second ends of the adjacent securing mechanisms.

Additionally or alternatively to any of the above, non-limiting examples, the one or more securing mechanisms may be made of a flexible material.

Additionally or alternatively to any of the above, the flexible material may comprise nitinol.

A seventh illustrative and non-limiting example is an implantable medical device system that may comprise an implantable pulse generator that may comprise a canister housing operational circuitry adapted to generate a therapy output, a lead adapted for coupling to the implantable pulse generator and adapted to deliver the therapy output from the implantable pulse generator, and a retention device as in any of the above non-limiting examples, wherein the lead may be sized and shaped to be received in the hollow lumen of the retention device.

A eighth illustrative and non-limiting example is a method of implanting an implantable lead in a patient that may comprise the use of an implantable lead that may have a first end for coupling to an implantable medical device and a second end for implantation at a target site in the patient, with a lead body extending therebetween and a retention device for use with an implantable medical device (IMD), the retention device as in any of the above non-limiting examples. The method may include inserting the implantable lead into the patient with the retention device placed on the lead at a desired location thereon and with a sheath disposed about at least a portion of the lead and compressing the one or more securing mechanisms of the retention device in a delivery configuration. The method may also include at least partly withdrawing the sheath such that the one or more securing mechanisms extend to a deployed configuration to anchor the implantable lead to tissue of the patient.

Additionally or alternatively to the eighth illustrative, non-limiting example, the step of inserting the implantable lead may be performed by making a first incision and a second incision, making a first tunnel between the first and second incisions, making a second tunnel from the second incision to an end location, and passing at least the second end of the implantable lead through the second incision to the end location, wherein the step of inserting the implantable lead may be performed such that the retention device may be accessible near the second incision, and the method may further comprise positioning the retention device near a xiphoid of the patient and partly withdrawing the sheath allowing the one or more securing mechanisms to extend to the deployed configuration and push against tissue of the patient near the second incision to secure the lead in a selected position.

Additionally or alternatively to any of the above, non-limiting examples, the implantable lead may be inserted through at least one of the tunnels by advancing a portion of the implantable lead into and through a sheath that has already been placed in the tunnel.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 1A-1B show a first example retention device;

DETAILED DESCRIPTION

The following detailed description should be read with reference to the drawings. The drawings, which are not necessarily to scale, depict illustrative embodiments and are not intended to limit the scope of the invention. Any references to other patents or patent applications are intended as illustrative of useful methods or devices and are not intended to foreclose suitable alternatives. In the methods shown below, structures may be beneath the skin and over the ribcage of the patient, though such elements are not always shown in phantom. Some examples may place devices in the abdomen, again making use of anchoring techniques that secure to the fascia.

The words "proximal" and "distal" are used herein to differentiate the ends of devices. No specific anatomical significance is intended. For example, the distal end of a lead is not necessarily anatomically distal relative to the proximal end of the lead; anatomic distal and proximal position will be determined by the final implantation location(s).

Figure 1B:
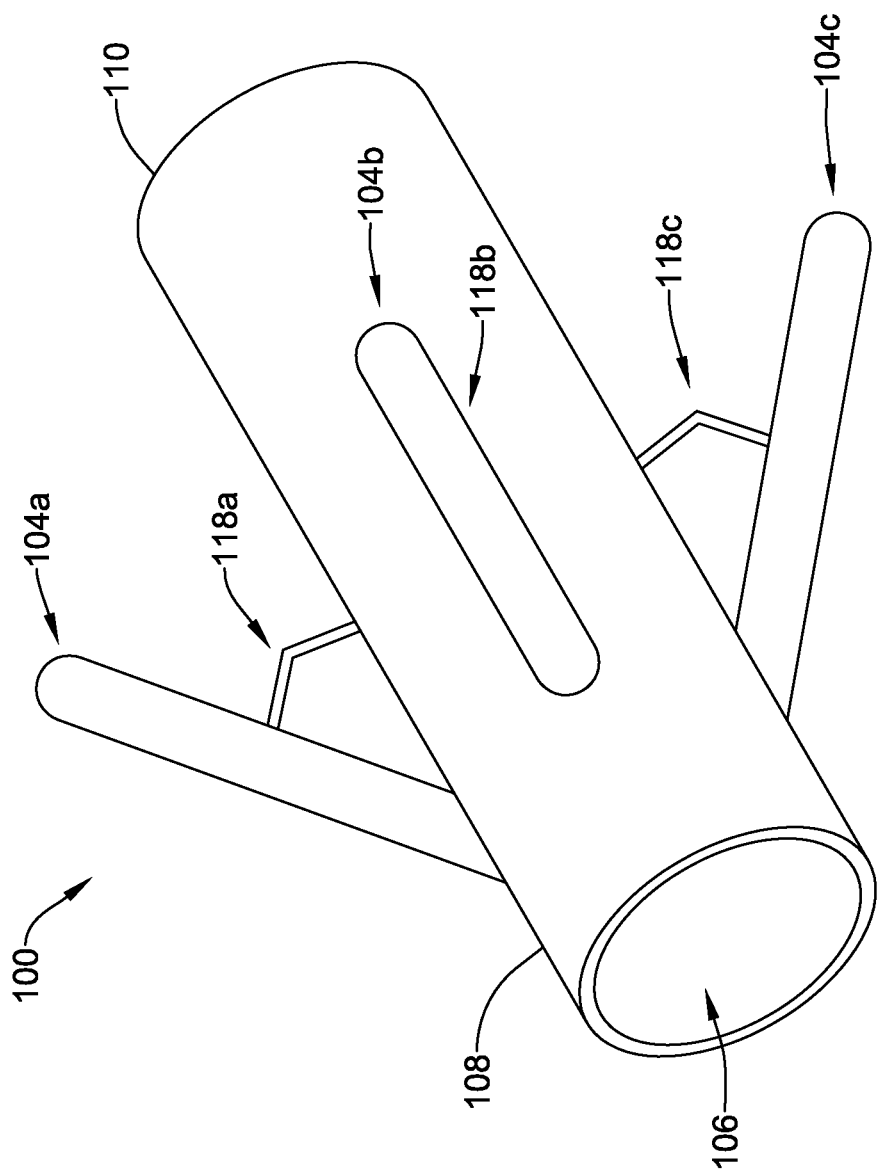

FIG. 1A depicts an illustrative side-view of an example retention device 100 and FIG. 1B depicts an illustrative isometric-view of the example retention device 100. As shown, the retention device 100 may include an elongate body 102 and securing mechanisms 104A-104C spaced circumferentially around the elongate body 102. In some cases, the elongate body 102 may have a hollow lumen 106 that extends from an open distal end 108 to an open proximal end 110. In an example, the hollow lumen 106 is dimensioned to receive a portion of an implantable lead therein. The elongate body 102 may be formed from any material suitable for chronic implantation in patients, such as a wide variety of plastics and/or metals. Different parts may be made of different materials, or may have additional structure, such as by using coated wires for the securing mechanisms and an extruded tube for the elongate body, or the entire piece may be formed in a single molding step of a single material.

The securing mechanisms 104A-104C are designed for securing the device 100 in a patient's tissue, such as in the subcutaneous space over the ribcage, or elsewhere. In some cases, the securing mechanisms 104A-104C are solely relied upon to anchor the device 100 to tissue of a patient; in other examples, a suture may also be used to augment securing force temporarily or permanently. While one set of securing mechanisms is shown, in other examples, there may be multiple sets of securing mechanisms spaced longitudinally along the elongate body 102.

In some cases, the securing mechanisms 104A-104C may be flaps that are a formed, single-piece with the elongate body 102 such as by injection molding or insert molding the entire piece onto a wire "skeleton". Alternatively, the securing mechanisms 104A-104C may have first ends 112A-112C coupled to the elongate body 102 in any suitable manner, which may include hinges, screws, pins and/or any other suitable fastener. In some cases, the first ends may be molded onto the elongate body 102.

In some cases, the securing mechanisms may be configured to shift or flex so that second ends 114A-114C of the securing mechanisms 104A-104C move, retract, or compress towards the elongate body 102 to a delivery configuration. In some cases, the securing mechanisms 104A-104C may be further configured to shift or flex so that the second ends 114A-114C move, swing, or extend away from the elongate body 102 to a deployed configuration. While in a deployed configuration, the second ends 114A-114C may be configured to push against the tissue of the patient when the retention device 100 is implanted in the patient.

The securing mechanisms may further comprise intermediate portions 116A-116C extending between the first and second ends. In the example shown, linking elements 118A-118C have first ends 120A-120C coupled to the elongate body 102 and second ends 122A-122C coupled to the intermediate portions 116A-116C of the securing mechanisms 104A-104C. The linking elements 118A-118C are flexible to allow the securing mechanisms to be compressed to their delivery configuration. In some cases, the linking elements 118A-118C may also have intermediate portions 124A-124C that include joints or bends configured to flex or shift and allow the securing mechanisms 104A-104C to move from the delivery configuration to the deployed configuration and limit or stop the securing mechanisms 104A-104C from moving beyond the deployed configuration. In some cases, because the securing mechanisms are reinforced by the linking elements to limit movement of the securing mechanisms while in the deployed configuration, the linking elements may prevent prolapse of the securing mechanisms when the retention device 100 is implanted within the patient.

In various examples, the securing mechanisms 104A-104C may be comprised of the same materials as the elongate body 102. However, in some cases, the securing mechanisms 104A-104C may be comprised of different materials than the elongate body 102. In certain embodiments, the securing mechanisms 104A-104C may be comprised of a different, stiffer, material than the elongate body 102. Alternatively, the securing mechanisms may be softer than the elongate body 102. In some examples, the securing mechanisms may be formed of silicone while a different polymer of stiffer or harder character is used for the elongate body 102. In other examples, the securing mechanisms may be coated or uncoated nitinol or other metal, making them generally stiffer than the elongate body. Moreover, in some examples, the securing mechanisms 104A-104C themselves may be comprised of different material (i.e., the linking elements 118A-118C may be comprised of softer and/or more flexible material than the rest of the securing mechanisms). In some cases, the securing mechanisms 104A-104C may be radiopaque.

According to various embodiments, the securing mechanisms 104A-104C may be arranged to enable the retention device 100 to be collapsed by a sheath to the delivery configuration. When the retention device 100 is in a selected position or configuration during implantation in the patient, the sheath may be removed. Upon removal of the sheath, the securing mechanisms 104A-104C may expand at least in a radial direction to engage, push against, and/or anchor the retention device 100 in a desired location such as the subcutaneous tissue of a patient. In some examples anchoring is desirable near the xiphoid of the patient, for example. In other examples anchoring is desirable in a substernal implantation position, wherein the anchoring apparatus is placed behind the sternum in the mediastinum, preferably without contacting the heart or lungs.

In one example, a shape memory material is used for the securing mechanisms 104A-104C, such that the delivery configuration may be achieved with little tension exerted by the securing mechanisms 104A-104C until body temperature is reached during implantation. Implantation may be performed using a sheath over the securing mechanisms 104A-104C to retrain them in the delivery configuration. Once implanted and with the insertion sheath removed, the shape memory material can then cause the securing mechanisms to spring outward, anchoring to the surrounding tissue.

In some instances, the securing mechanisms 104A-104C may be tine shaped, hook shaped, fan shaped, a combination thereof, etc. Furthermore, the securing mechanisms 104A-104C may have rounded second ends 114A-114C to encourage tissue anchoring without piercing through the skin or other sensitive anatomical structures. In other embodiments, the second ends 114A-114C may be square, pointed, convex, barbed, etc.

In some cases, as depicted in FIGS. 1A and 1B, there may be several securing mechanisms 104A-104C that are circumferentially spaced from one another around the elongate body 102. In some cases, the securing mechanisms 104A-104C may be limited to one side of the elongate body 102. In some instances, there may be a single securing mechanism 104A.

In some examples, the shapes of the securing mechanisms 104A-104C may vary from one another. For example, different ones of the securing mechanisms 104A-104C may have different lengths or widths from one another. Some may be tapered, barbed, and/or pointed, while others may have a different shape such as being rounded. In some examples such as that shown, the securing mechanisms 104A-104C may all have the same width, length and shape.

In some examples, the securing mechanisms 104A-104C may be attached to the elongate body 102 by the linking elements 118A-118C such that the securing mechanisms 104A-104C have a predefined desired degree of angular separation with the elongate body 102 in the deployed configuration. For example, the linking elements may be configured to stop the securing mechanisms from extending beyond predefined angle of separation from the elongate body, in the range of about 10° to about 60°, or in an example, about a 20° angle of separation with the elongate body 102. In some cases, the angle of separation may be 15°, 30°, 45°, 60° or more. In an example, the angle of separation may be less than 90°, preventing prolapse.

In some cases, the angles of separation may be substantially the same or equal across each of the securing mechanisms 104A-104C. In some cases, the angles of separation may not be the same or equal to one another. Thus, while the examples shown generally have sets of securing mechanisms 104A-104C that are symmetrically placed about the circumference of the retention device 100 with similar angular and shape characteristics, this need not be the case and different ones of the securing mechanisms 104A-104C may be differently oriented, sized or shaped, if desired. In addition, different ones of the securing mechanisms 104A-104C may have differing material properties, if desired. The various noted variations in shape, quantity, distribution, size, orientation, angular configuration, etc. may be incorporated in any of the following illustrative examples.

Figure 1C:
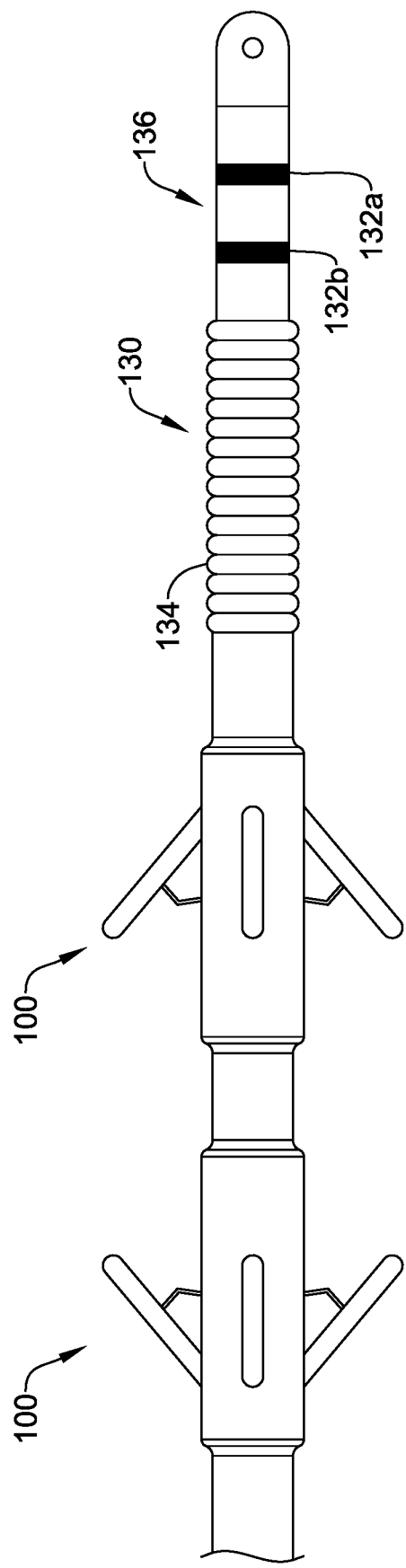
FIG. 1C shows the first example retention devices coupled to a lead.

FIG. 1C depicts the example retention device 100 coupled to an illustrative implantable lead 130. In some cases, as shown in FIG. 1C, the retention device may be coupled to the implantable lead 130 by placing the implantable lead 130 through the hollow lumen 106 of the retention device 100 such that the retention device 100 substantially surrounds the lead 130. In some examples, the lead 130 may include ring electrodes illustrated at 132A, 132B as well as coil electrode 134, though other electrode types and quantities may be used. For example, a directional electrode array may be used. The lead 130 may be manufactured of any suitable material and by any suitable manner. As noted above, a sheath may be disposed over the retention device 100 prior to or during implantation.

Figure 1D:
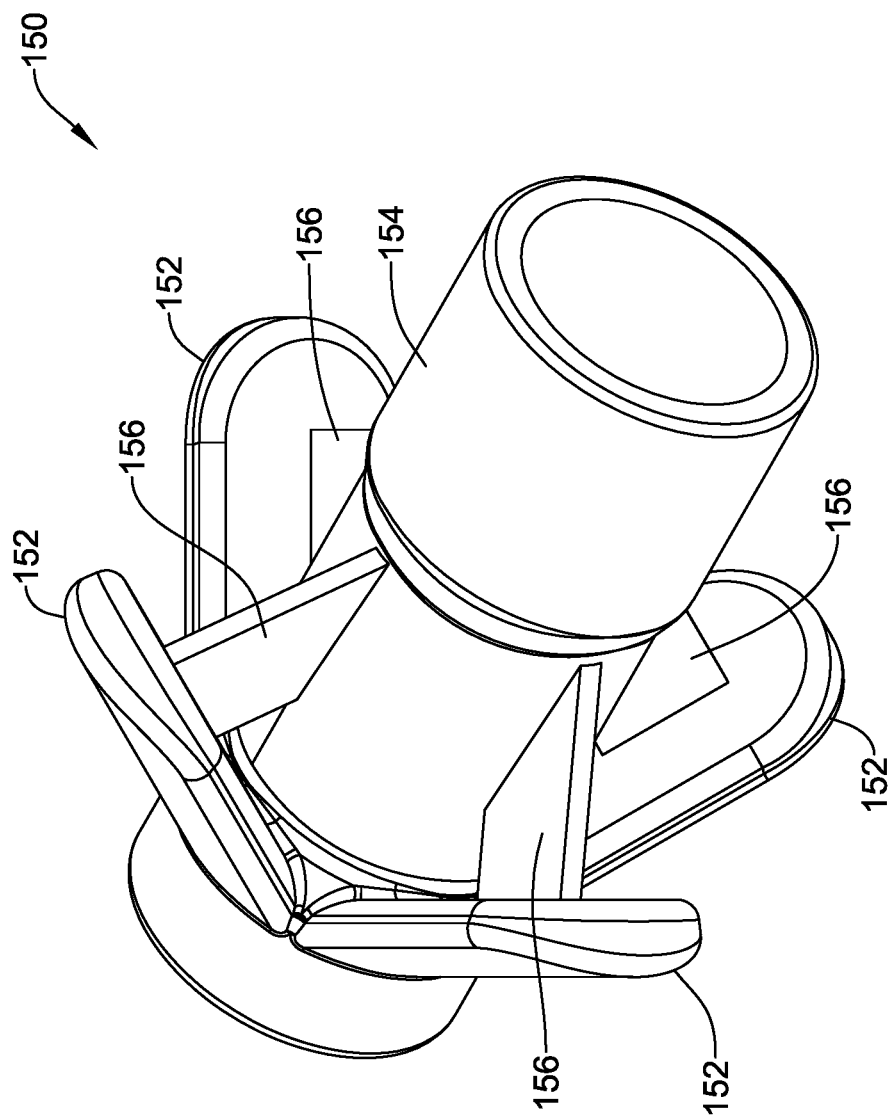
FIG. 1D shows an alternative design for the first example retention device.

FIG. 1D depicts an illustrative view of another example retention device 150. As shown, the retention device 150 may include an elongate body 154 and securing mechanisms 152 spaced circumferentially around the elongate body 154, and a hollow lumen extending from an open distal end to an open proximal end. Various elements of the materials, construction and/or purpose of operation of the retention device 150 may be similar to that of the retention device 100. However, in this example, the securing mechanisms 152 may include linking elements 156 that may be elongate and configured to slide down into the hollow lumen such that the securing mechanisms 152 can fold down and lay relatively flat against the elongate body 154 when the retention device 150 is in the delivery configuration. For instance, the elongate body 102 may include gaps or holes that extend from a surface of the elongate body 154 to the hollow lumen. Additionally, the linking elements 156 may have first ends that fit into the gaps of the elongate body 154 and second ends coupled to the securing mechanisms 152. In some cases, the linking elements may slide into the gaps of the elongate body 154 and into the hollow lumen to allow the securing mechanisms to be compressed to their delivery configuration. In some cases, the linking elements may also slide out from the hollow lumen to allow the securing mechanisms to move from the delivery configuration to the deployed configuration. In some examples, the linking elements may be configured to stop from completely sliding out of the gaps and limit or stop the securing mechanisms from moving beyond the deployed configuration. In some cases, because the securing mechanisms are reinforced by the linking elements to limit movement of the securing mechanisms while in the deployed configuration, the linking elements may prevent prolapse of the securing mechanisms when the retention device 150 is implanted within the patient.

Figure 2A:
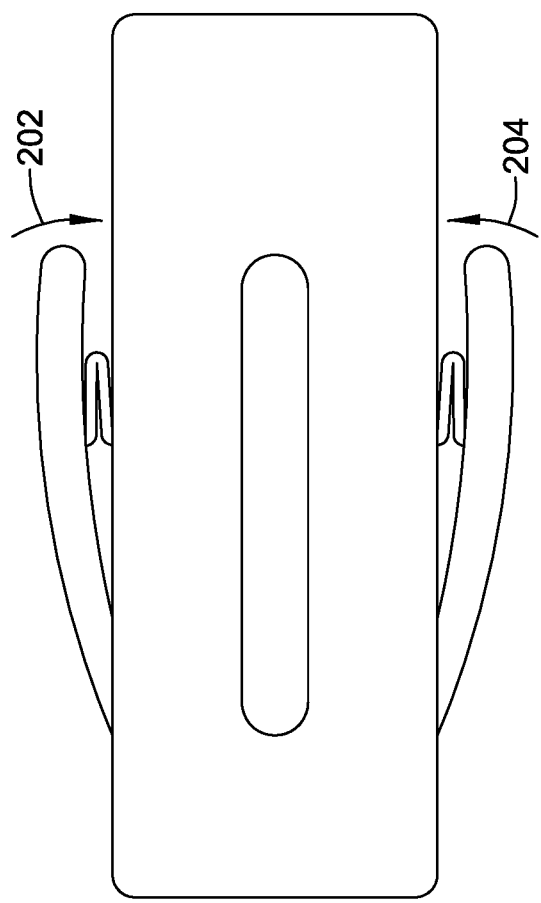
FIG. 2A shows the first example retention device in a delivery configuration.
Figure 2B:
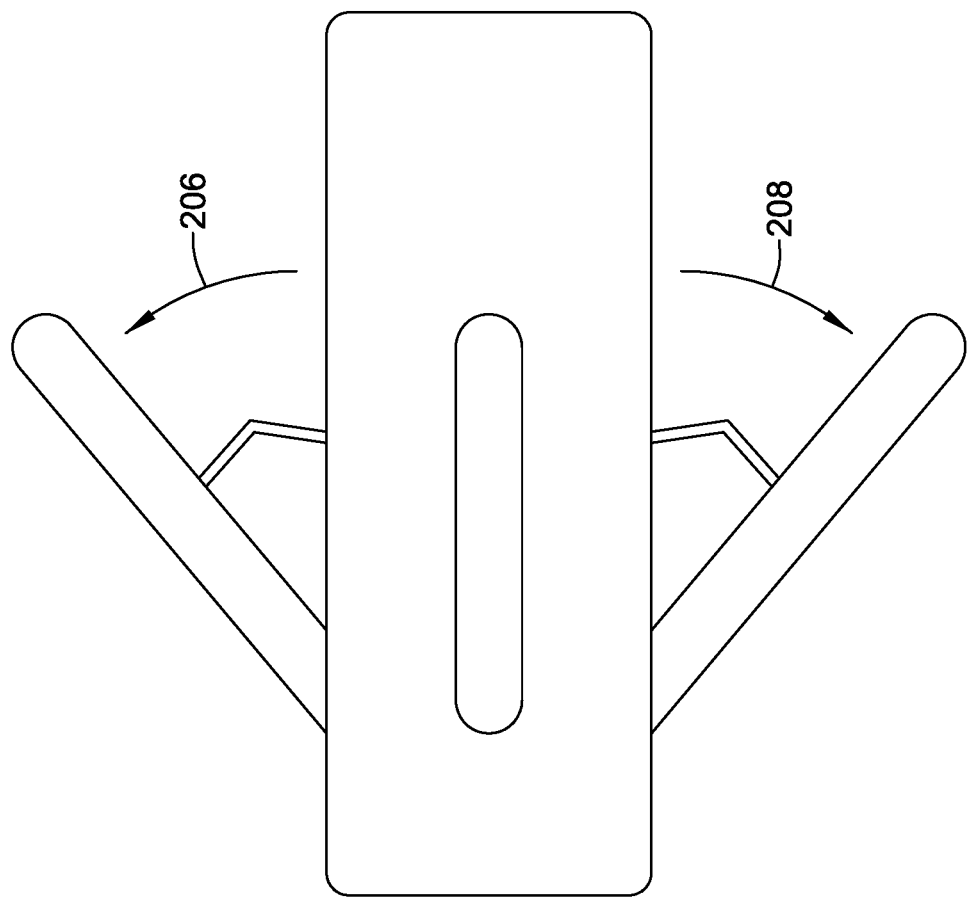
FIG. 2B shows the first example retention device in a deployed configuration.

FIGS. 2A and 2B depict an illustrative example of the securing mechanisms 104A-104C moving the retention device 100 from the delivery configuration (depicted in FIG. 2A) to the deployed configuration (depicted in FIG. 2B). As shown in FIG. 2A, when the securing mechanisms are collapsed by a sheath and/or shape memory techniques, to the deployed configuration, the linking elements 118A-118C may bend or collapse (as shown by arrows 202 and 204) such that the securing mechanisms lay relatively flat against the elongate body 102. Moreover, as shown in FIG. 2B, when the retention device 100 is at a desired position within the patient, the sheath may be removed and securing mechanisms may bend or expand to the deployed configuration (as shown by arrows 206 and 208) such that the securing mechanisms extend at least in the radial direction to a predefined angle away from the elongate body, with the linking elements limiting the degree of separation of the securing mechanisms relative to the device body.

Referring to FIGS. 1A and 2A, the intermediate joints or bends 124A-124C may be omitted in some embodiments. Rather than folding down as shown in FIG. 2A, the linking elements 118A-118C and securing mechanisms 104A-104C may more or less wrap around the elongate body 102 to assume a collapsed configuration. The thickness, along the axial dimension of the elongate body, of the linking elements 118A-118C may be larger than that shown. For example, the linking elements 118A-118C shown in FIG. 1A-1C have a thickness in the axial direction 119 of the elongate body 102 that is in the range of less than 10% of the length of the securing mechanisms 104A-104C. Thickness 119 may be, in other examples, in the range of 10% to 50% of the length of the securing mechanisms 104.

Figure 3A:
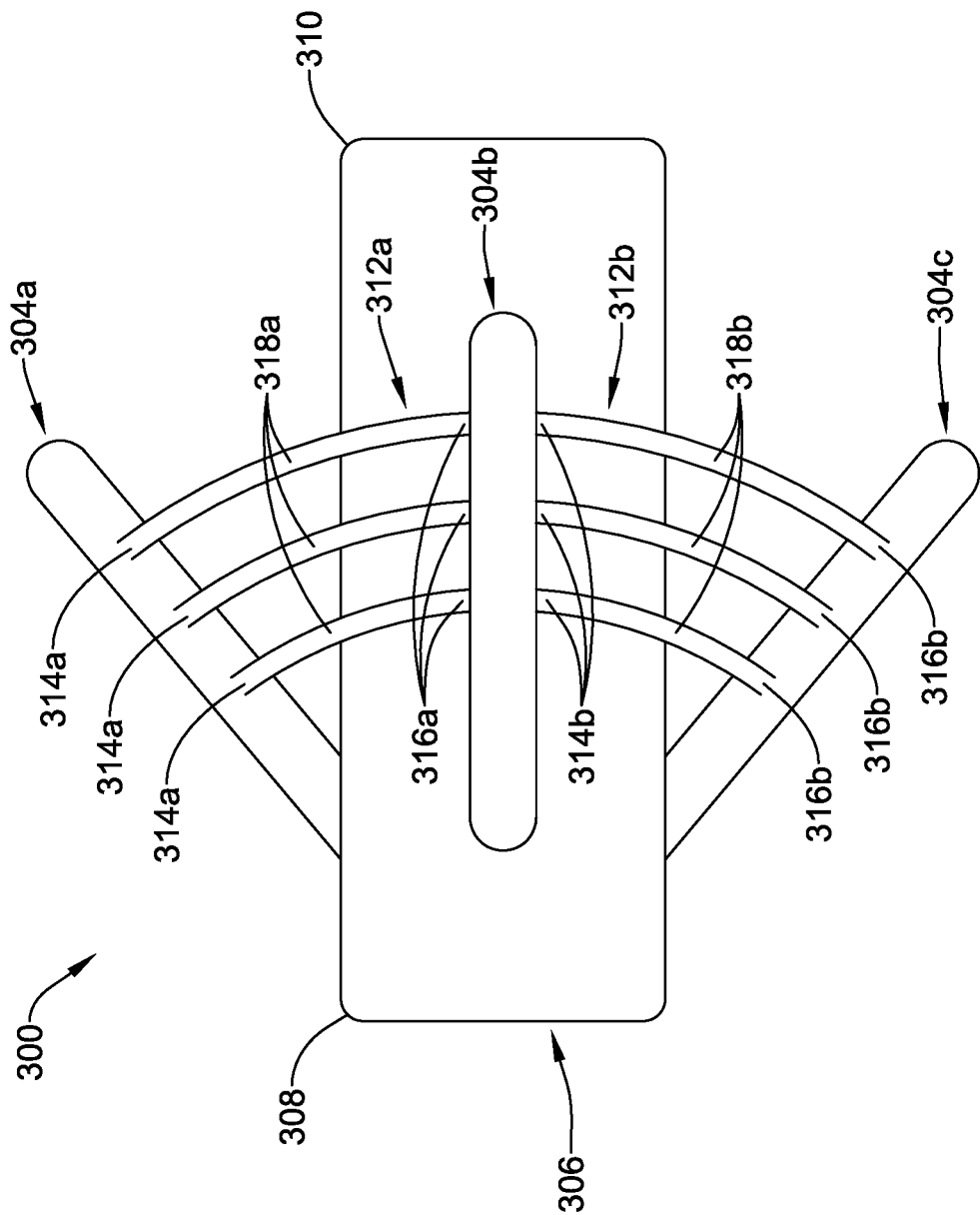
FIGS. 3A-3B show a second example retention device.
Figure 3B:
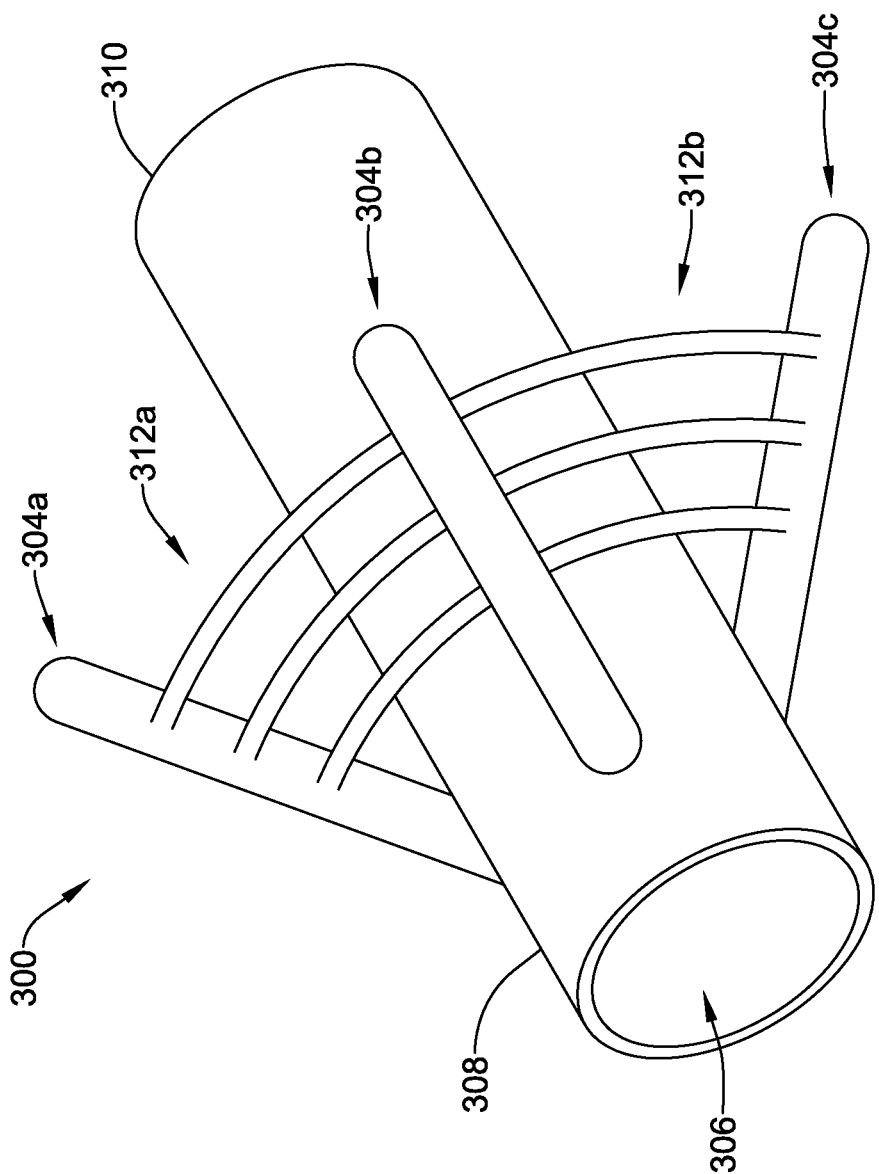

FIG. 3A depicts an illustrative side-view of another example retention device 300 and FIG. 3B depicts an illustrative isometric-view of the example retention device 300. As shown, the retention device 300 may include an elongate body 302 and securing mechanisms 304A-304C spaced circumferentially around the elongate body 302, and a hollow lumen 306 extending from an open distal end 308 to an open proximal end 310. Various elements of the materials, construction and/or purpose of operation of the retention device 300 may be similar to that of the retention device 100. However, in this example, the securing mechanisms 304A-304C may include linking elements 312A-312B that assist the securing mechanism to facilitate their purpose of operation. For instance, the linking elements 312A-312B may have first ends 314A-314B coupled to one of the securing mechanisms and second ends 316A-316B coupled to another securing mechanism (e.g., an adjacent securing mechanism). To some extend the design defines a web. In some cases, the linking elements 312A-312B may also have intermediate portions 318A-318B configured to bend or flex to allow the securing mechanisms 304A-304C to move from the delivery configuration to the deployed configuration and limit or stop the securing mechanisms 304A-304C from moving beyond the deployed configuration. In some cases, because the securing mechanisms are reinforced by the linking elements and hold the securing mechanisms from moving beyond a desired angle in the deployed configuration, the linking elements may prevent prolapse of the securing mechanisms when the retention device 300 is implanted within the patient. In another example, the linking elements may help to push the securing mechanisms to the deployed position once a constraining sheath is removed.

Figure 3C:
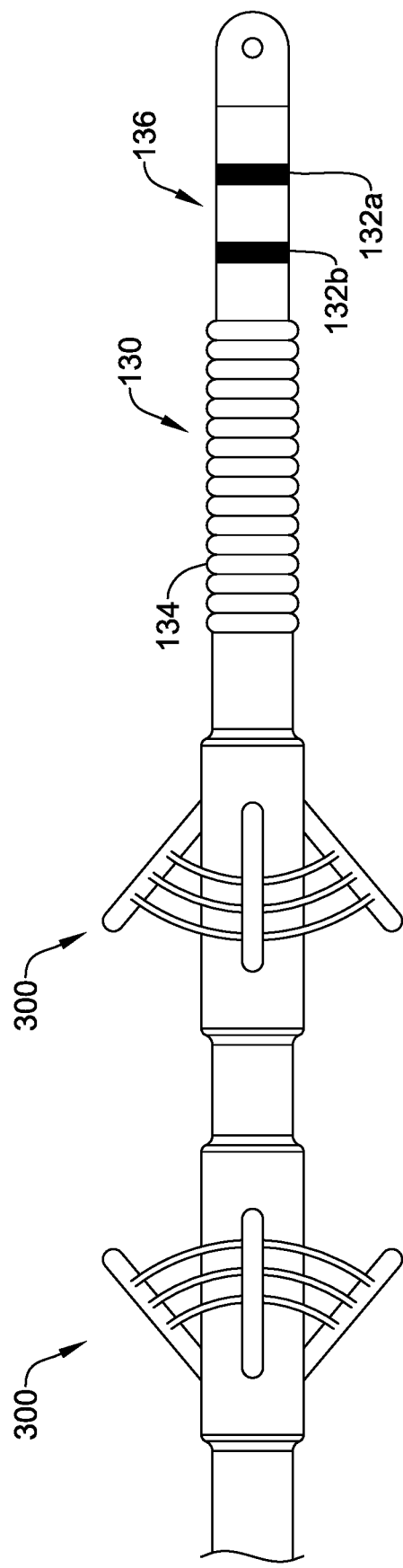
FIG. 3C shows the second example retention devices coupled to the lead.

FIG. 3C depicts the example retention device 300 coupled to an illustrative implantable lead 130. In some cases, as shown in FIG. 3C, the retention device may be coupled to the implantable lead 130 by placing the implantable lead 130 through the hollow lumen 306 of the retention device 300 such that the retention device 300 substantially surrounds the lead 130. As noted above, a sheath may be disposed over the retention device 300 prior to or during implantation.

Figure 4A:
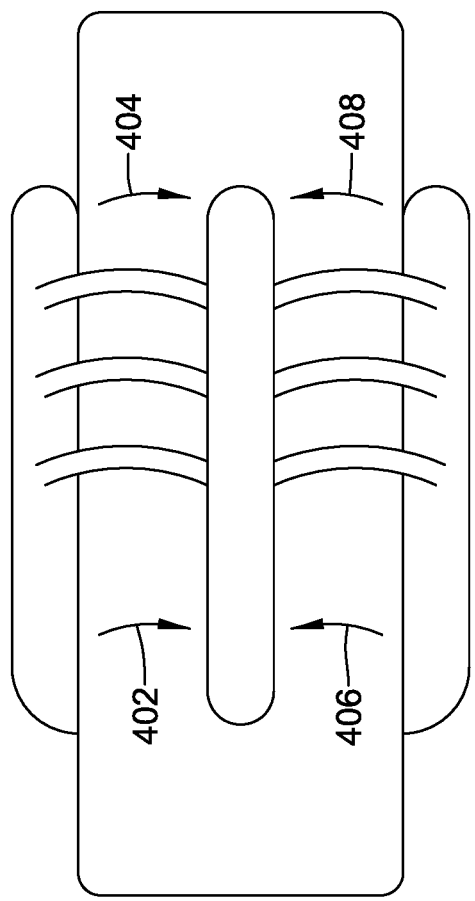
FIG. 4A shows the second example retention device in a delivery configuration.
Figure 4B:
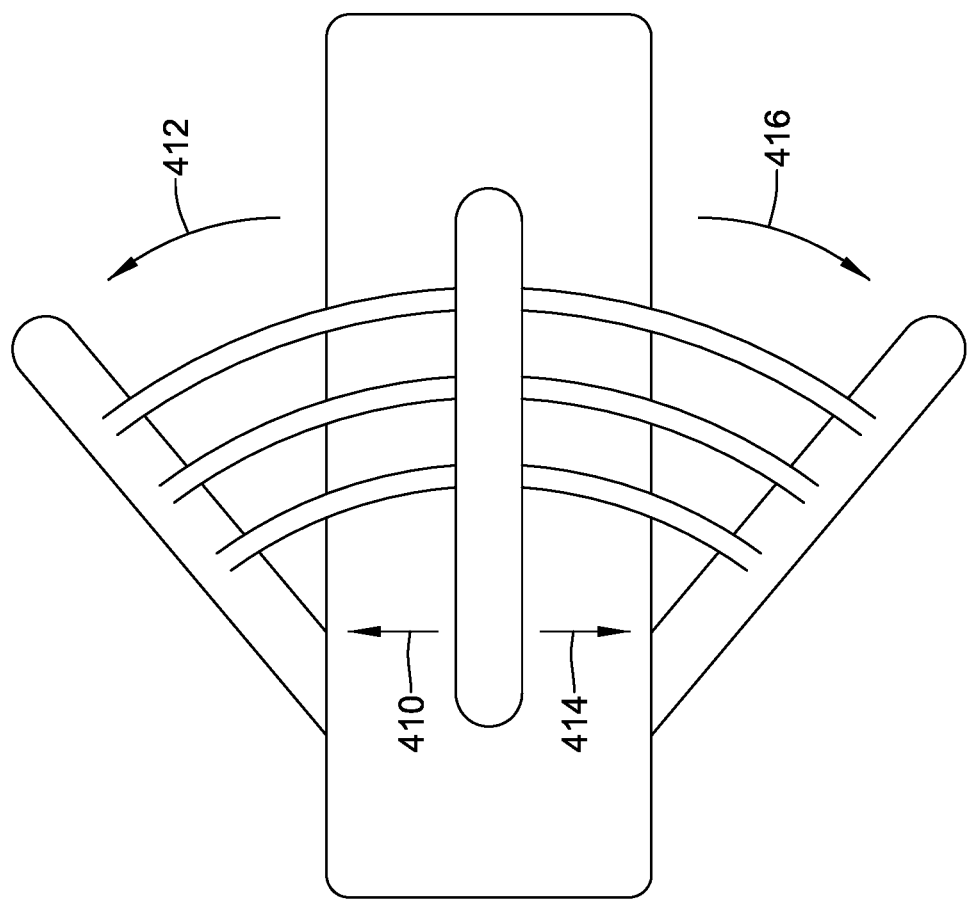
FIG. 4B shows the second example retention device in a deployed configuration.

FIGS. 4A and 4B depict an illustrative example of the securing mechanisms 304A-304C moving the retention device 300 from the delivery configuration (depicted in FIG. 4A) to the deployed configuration (depicted in FIG. 4B). As shown in FIG. 4A, when the securing mechanisms are collapsed by a sheath and/or shape memory techniques to the delivery configuration, the linking elements 312A-312B may bend or collapse (as shown by arrows 402-408) such that the securing mechanisms lay relatively flat against the elongate body 302.

As shown in FIG. 4B, when the retention device 300 is at a desired position within the patient, the sheath may be removed and the linking elements may straighten or expand to the deployed configuration (as shown by arrows 410-416) such that the securing mechanisms extend at least in the radial direction to a predefined angle away from the elongate body. Alternatively, the securing mechanisms themselves may reshape to adopt a deployed configuration, with the linking elements limiting motion thereof to prevent prolapse.

Figure 5A:
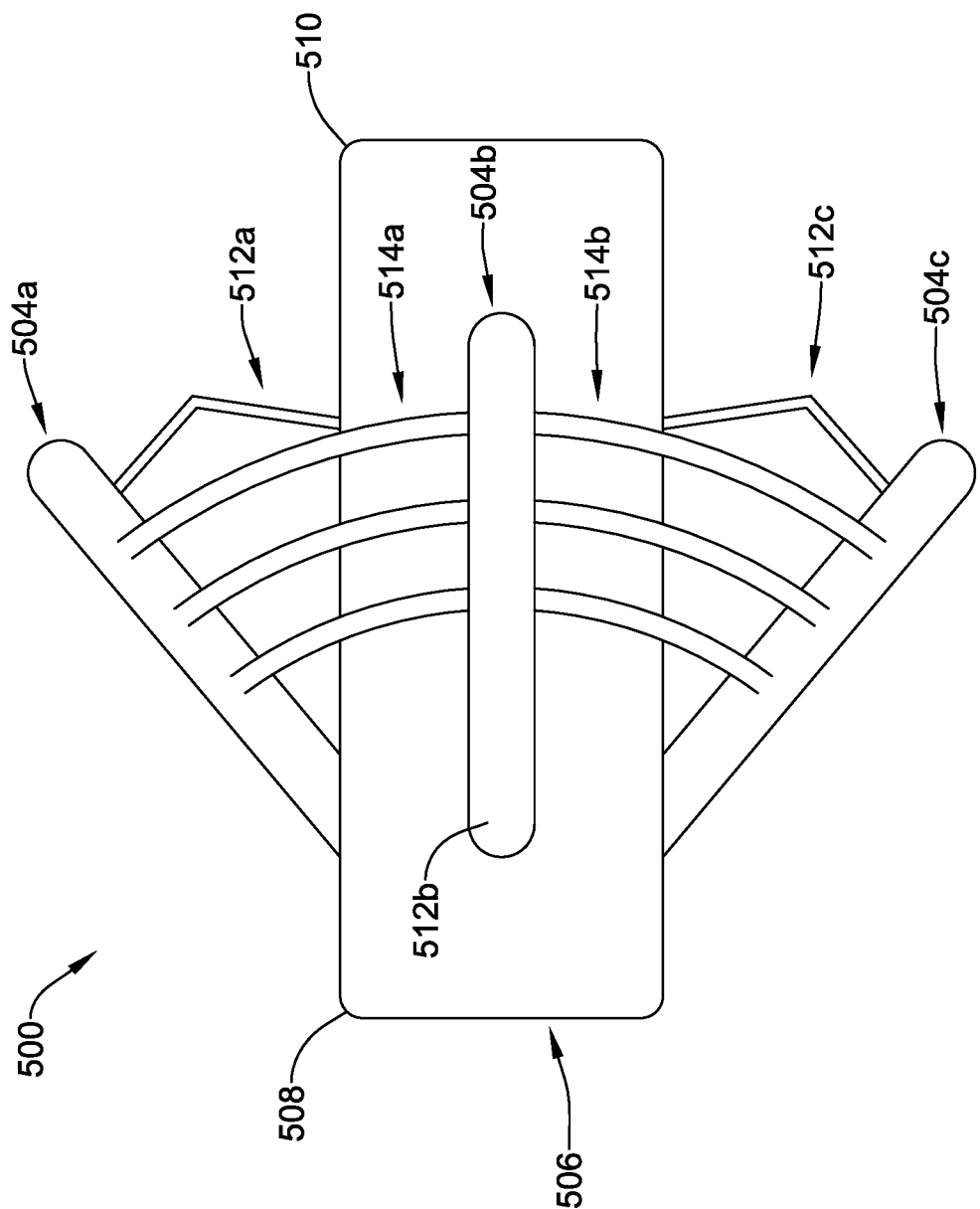
FIGS. 5A-5B show a third example retention device.
Figure 5B:
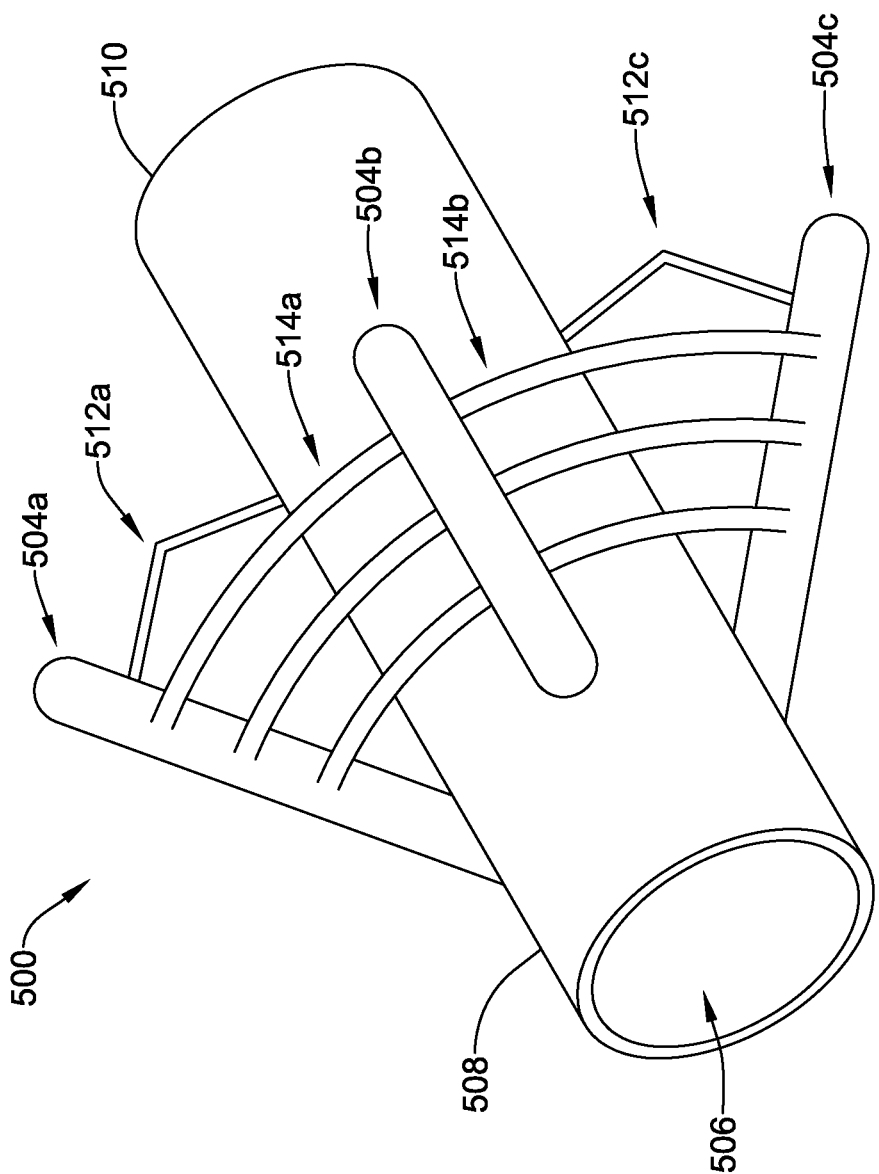

FIG. 5A depicts an illustrative side-view of another example retention device 500 and FIG. 5B depicts an illustrative isometric-view of the example retention device 500. This example combines elements of retention devices 100 and 300. The retention device 500 may include an elongate body 502, securing mechanisms 504A-504C spaced circumferentially around the elongate body 502, and a hollow lumen 506 extending from an open distal end 508 to an open proximal end 510. The overall material and purpose of operation of the retention device 500 may be similar to that of the retention device 100 and 300. In this example, the securing mechanisms 504A-504C may include both linking elements 512A-512C and 514A-514C that assist the securing mechanism to facilitate their purpose of operation.

In the example, the linking elements 512A-512C may be coupled to the securing mechanisms and the elongate body and include joints or bends configured to flex or shift and allow the securing mechanisms 504A-504C to move from the delivery configuration to the deployed configuration and limit or stop the securing mechanisms 504A-504C from moving beyond the deployed configuration. In addition, linking elements 514A-514B may be coupled between two adjacent securing mechanisms and are configured to bend or flex to allow the securing mechanisms 504A-504C to move between the delivery configuration and the deployed configuration. The combination of linking elements 512A-512C and the linking elements 514A-514B and hold the securing mechanisms in a desired position, preventing prolapse while also keeping a larger profile of the overall anchoring structure than if, for example, the securing mechanisms could all collapse to one side of the device. Meanwhile, as prolapse is prevented, and overall extension away from the elongate body 502 is limited, the individual ones of the securing mechanisms 504A-504C may be prevented from puncturing the skin or other nearby anatomy. Thus for example, an anchoring device as depicted may be helpful in positions in the mediastinum (such as for a substernal cardiac device) and/or near the spine (such as for a neuromodulation device or for a subcutaneous defibrillator having a posterior lead), where nearby structures (heart, lung, and/or spinal cord) should be protected.

Figure 5C:
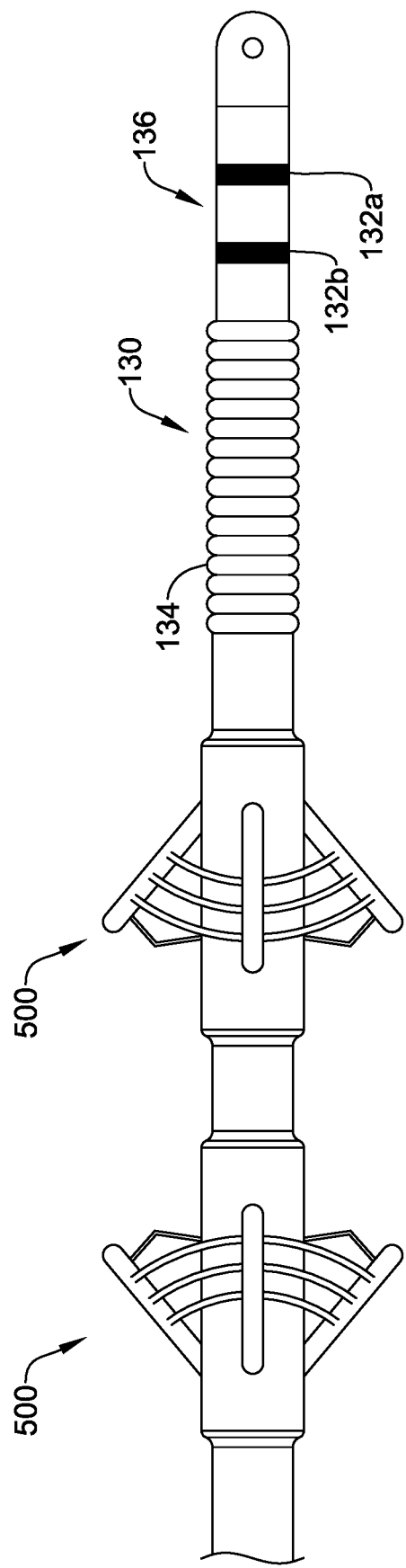
FIG. 5C shows the third example retention devices coupled to the lead.

FIG. 5C depicts the example retention device 500 coupled to an illustrative implantable lead 130. In some cases, as shown in FIG. 5C, the retention device may be coupled to the implantable lead 130 by placing the implantable lead 130 through the hollow lumen 506 of the retention device 500 such that the retention device 500 substantially surrounds the lead 130. As noted above, a sheath may be disposed over the retention device 500 prior to or during implantation.

Figure 6A:
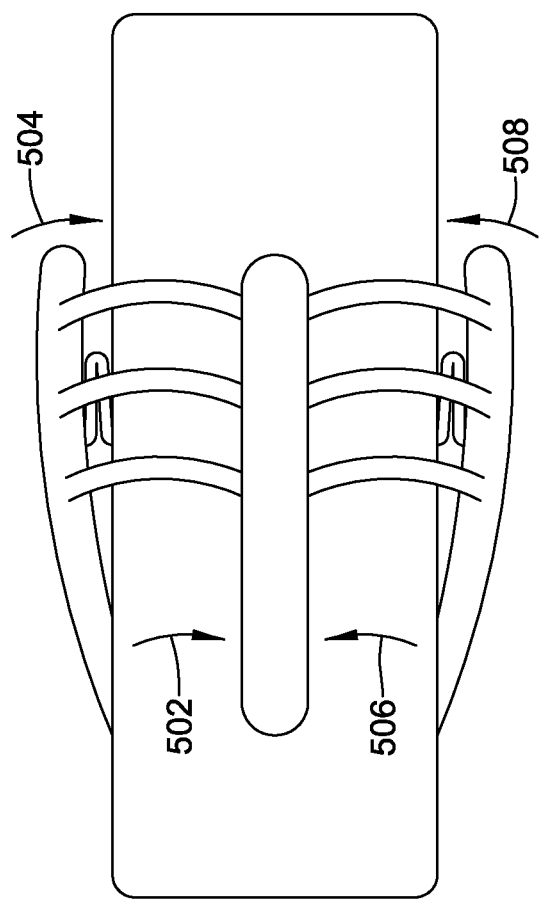
FIG. 6A shows the third example retention device in a delivery configuration.
Figure 6B:
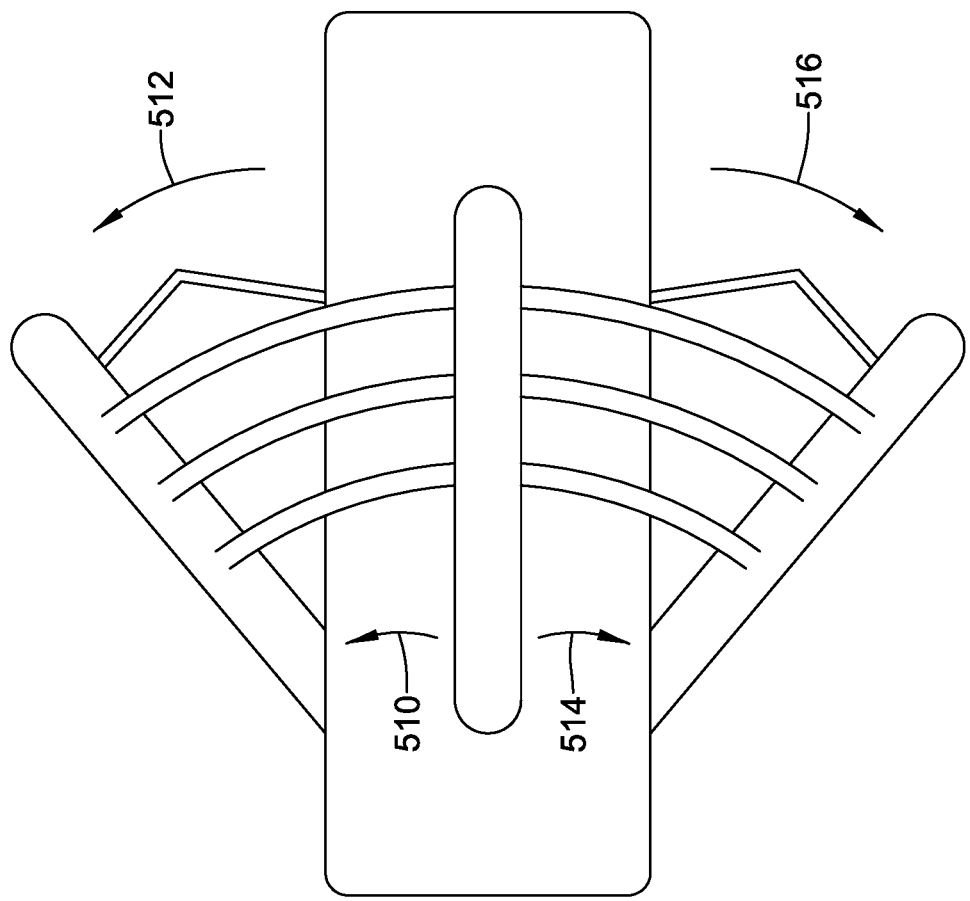
FIG. 6B shows the third example retention device in a deployed configuration.

FIGS. 6A and 6B depict an illustrative example of the securing mechanisms 504A-504C moving the retention device 500 from the delivery configuration (depicted in FIG. 6A) to the deployed configuration (depicted in FIG. 5B). As shown in FIG. 5A, when the securing mechanisms are collapsed by a sheath and/or shape memory techniques to the delivery configuration, the linking elements 512A-512B and 514A-514B may bend or collapse such that the securing mechanisms lay relatively flat against the elongate body 502. Moreover, as shown in FIG. 6B, when the retention device 500 is at a desired position within the patient, the sheath may be removed and the linking elements may straighten or expand as the securing mechanisms move to the deployed configuration. Force for such explanation to the deployed configuration may be provided by any of the securing mechanisms or linking elements.

Figure 7A:
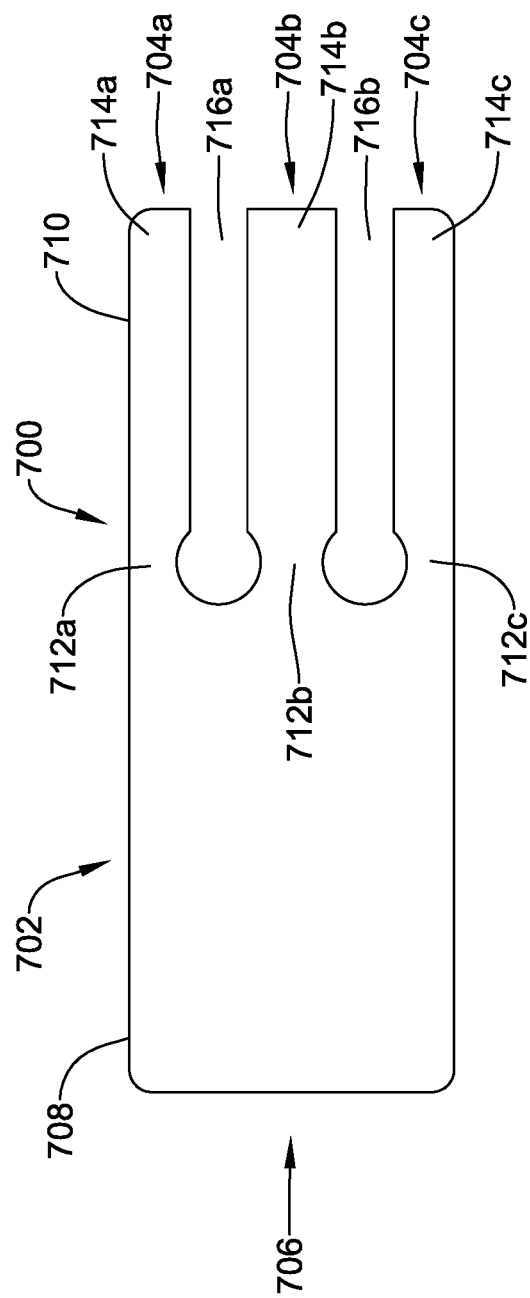
FIG. 7A shows a fourth example retention device in a delivery configuration.

FIG. 7A depicts an illustrative side-view of another example retention device 700 in a delivery configuration. As shown, the retention device 700 may include an elongate body 702 and securing mechanisms 704A-704C. In some cases, the retention device 700 may have a hollow lumen 706 that extends from an open distal end 708 to an open proximal end 710. In an example, the hollow lumen 706 is dimensioned to receive a portion of an implantable lead therein.

The retention device 700 may be formed from any material suitable for chronic implantation in patients, such as a wide variety of plastics, metals, and/or metal alloys, such as nitinol, for example. Different parts may be made of different materials or additional structure of the retention device 700 may be produced using different techniques. For instance, a single nitinol piece having a generally tubular shape may be subject to laser cutting and austenite temperature shaping techniques to cut and/or form the securing mechanisms from an end of the tube. In various examples, the securing mechanisms 704A-704C may be comprised of the same materials as the elongate body 702. However, in some cases, the securing mechanisms 704A-704C may be comprised of different materials than the elongate body 702. In some instances, the securing mechanisms 704A-704C may be comprised of a different, stiffer, material than the elongate body 702. Alternatively, the securing mechanisms may be softer than the elongate body 702. Moreover, in some cases, the securing mechanisms 704A-704C may be radiopaque.

Figure 7B:
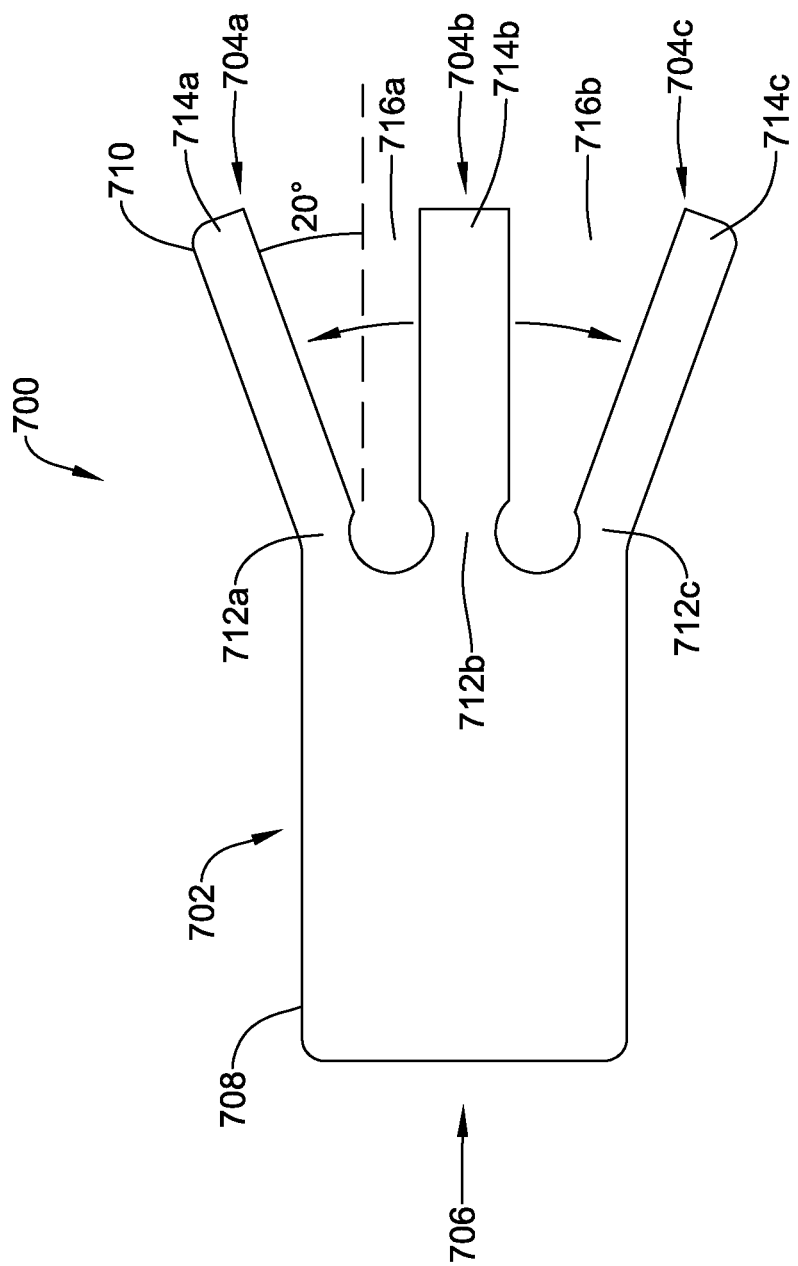
FIG. 7B shows the fourth example retention device in a deployed configuration.

FIG. 7B depicts an illustrative side-view of the example retention device 700 in a deployed configuration. In some cases, the securing mechanisms 704A-704C may have first ends 712A-712C configured to bend such that a portion of the securing mechanisms 704A-704C extend to a predefined angle relative to the elongate body 702. As shown in FIG. 7B, in this example, the securing mechanisms 704A-704C may extend around 20° relative to the elongate body 702. In some cases, the angle of separation may be in the range of about 10° to about 60°. In certain examples, the angle of separation may be about 15°, 30°, 45°, 60°, or 75°, for example. In some cases, the angles of separation may be substantially the same or equal across each of the securing mechanisms 704A-704C. In some cases, the angles of separation may not be the same or equal to one another. In some cases, the securing mechanisms 704A-704C may include second ends 714A-714C that may be configured to extend to the predefined angle and push against tissue of the patient when the retention device 700 is implanted in a patient. If desired, an outer web of intermediate pieces as shown above in the example of FIGS. 3A-3B may be provided with the securing mechanisms 704A-704C.

Figure 7C:
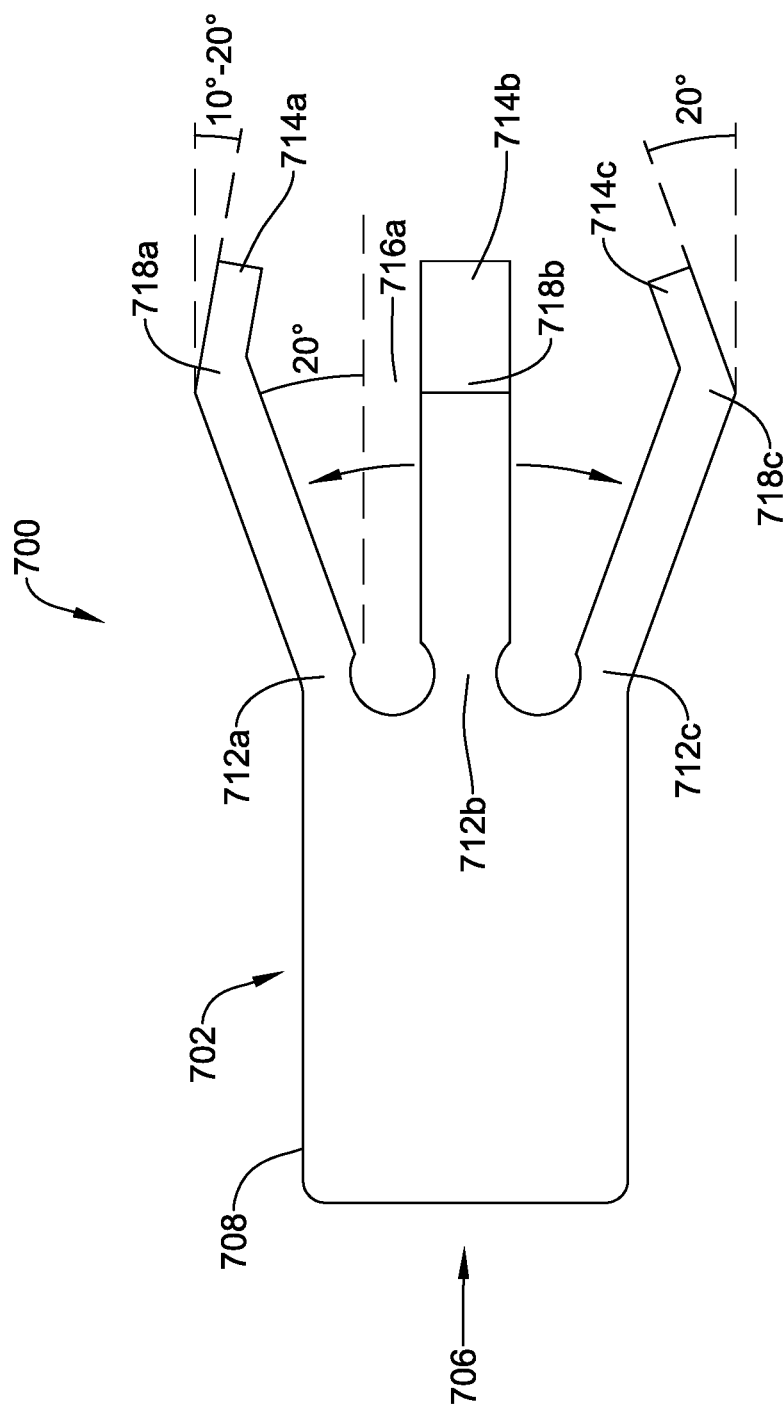
FIG. 7C shows an alternative version of the fourth example retention device in a deployed configuration.

FIG. 7C depicts an illustrative side-view of the example retention device 700 in another deployed configuration. In some cases, the first ends 712A-712C of the securing mechanism 704A-704C may be configured to bend and extend intermediate sections 718A-718C of the securing mechanisms 704A-704C to a first predefined angle relative to the elongate body 702 and the intermediate sections 718A-718C may also bend and extend the second ends 714A-714C to a second predefined angle relative to the elongate body 702. In some examples, the second predefined angle may be equal and opposite to the first predefined angle. However, this does not have to be the case. As shown in FIG. 7C, in this example, the second ends 714A-714C may extend around ~10°-20° relative to the elongate body 702. In some cases, the second angle of separation may be 15°, 30°, 45°, 60°, 90°, etc. In some cases, the angles of separation may be substantially the same or equal across each of the second ends 714A-714C. In some cases, the angles of separation may not be the same or equal to one another. In some cases, since the second ends 714A-714C may bend in the opposite direction of the first ends 712A-712, the intermediate sections 718A-718C may be configured to push against tissue of the patient when the retention device 700 is implanted in the patient. This configuration may encourage tissue anchoring without piercing through the skin or other sensitive anatomical structures since the extended intermediate sections may be less sharp the second ends of the securing mechanisms.

Turning back to FIG. 7A, as stated above, in some cases, the securing mechanisms 704A-704C may be flaps, leaflets, tines, hooks, fans, a combination thereof, etc. that are cut from the elongate body 702 such that the securing mechanisms 704A-704C are separated by gaps 716A-716B. In some examples, the gaps 716A-716B may be non-constant such that the first ends 712A-712C of the securing mechanism are separated by a larger distance from one another than the second ends 714A-714C, but this does not have to be the case. Furthermore, the securing mechanisms 704A-704C may have rounded second ends 714A-714C to encourage tissue anchoring without piercing through the skin or other sensitive anatomical structures. In other examples, the second ends 714A-714C may be square, pointed, convex, barbed, etc. in some examples, the shapes of the securing mechanisms 704A-704C may vary from one another. For example, different ones of the securing mechanisms 704A-704C may have different lengths or widths from one another. Some may be tapered, barbed, and/or pointed, while others may have a different shape such as being rounded. In some examples such as that shown, the securing mechanisms 704A-704C may all have the same width, length and shape. In some cases, as depicted in FIGS. 7A-7C, there may be several securing mechanisms 704A-704C that are circumferentially, spaced from one another around the elongate body 702. In some cases, the securing mechanisms 704A-704C may be limited to one side of the elongate body 702. In some instances, there may be a single securing mechanism 704A. Thus, while the examples shown generally have sets of securing mechanisms 704A-704C that are symmetrically placed about the circumference of the retention device 700 with similar angular and shape characteristics, this need not be the case and different ones of the securing mechanisms 704A-704C may be differently oriented, sized or shaped, if desired. In addition, different ones of the securing mechanisms 704A-704C may have differing material properties, if desired. The various noted variations in shape, quantity, distribution, size, orientation, angular configuration, etc. may be incorporated in any of the following illustrative to examples.

In some cases, when austenite temperature shaping techniques are used for the securing mechanisms 704A-704C, once the retention device 700 is implanted within the patient, the shape memory material can then cause the securing mechanisms 704A-704C to bend or flex at the first ends to the first predefined angle to the deployed configuration, as depicted in FIG. 7B. In other cases, the shape memory material can cause the securing mechanisms 704A-704C to bend or flex at the first ends to the first predefined angle and bend or flex at the intermediate sections to the second predefined angle to the deployed configuration, as depicted in FIG. 7C. In either deployed configuration, the retention device 700 may then be anchored in a desired location such as the subcutaneous tissue of the patient or near a xiphoid of the patient, for example.

In another example, a device as shown in FIGS. 7A-7C may comprise a nitinol or other metal base piece that is coated (for example, by spray, dip, overmold, etc.) with a polymer such as a silicone or other polymer that may reduce trauma. Moreover, any of the examples shown herein may be used in such a manner. Thus, for example, and without limitation, a device as in FIGS. 1A-1D, or FIGS. 2A-2B, or FIGS. 3A-3C, or FIGS. 4A-4B, or FIGS. 5A-5C, or FIGS. 6A-6B, or FIGS. 7A-7C, or FIGS. 8A-8C, or FIGS. 9A-9B, may include a coating, deposited by spray, dip, or molding onto a wire skeleton or a formed or assembled piece, tube or sheet of Nitinol or other metal, or even onto a resilient polymer, to provide a soft and biocompatible atraumatic exterior coating of silicone or other polymeric material.

Figure 8A:
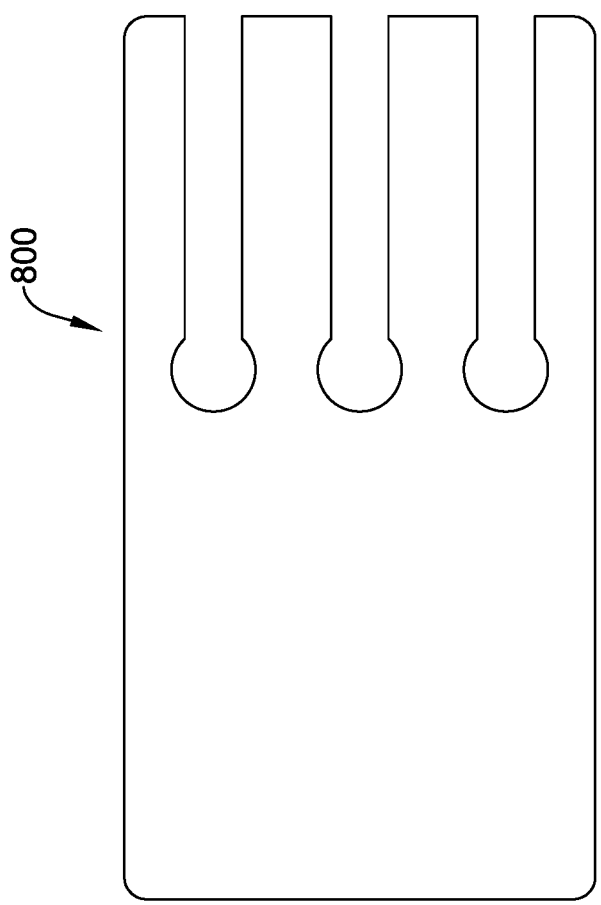
FIG. 8A shows a fifth example retention device in a delivery configuration.
Figure 8B:
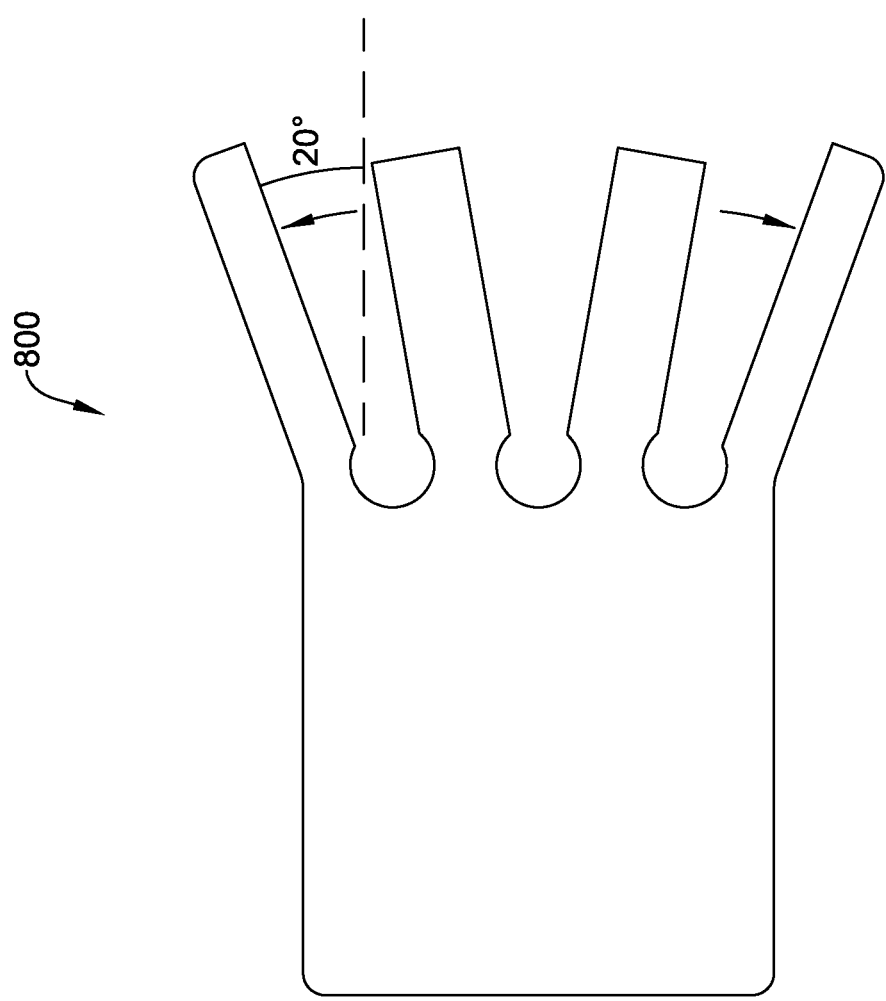
FIG. 8B shows the fifth example retention device in a deployed configuration.
Figure 8C:
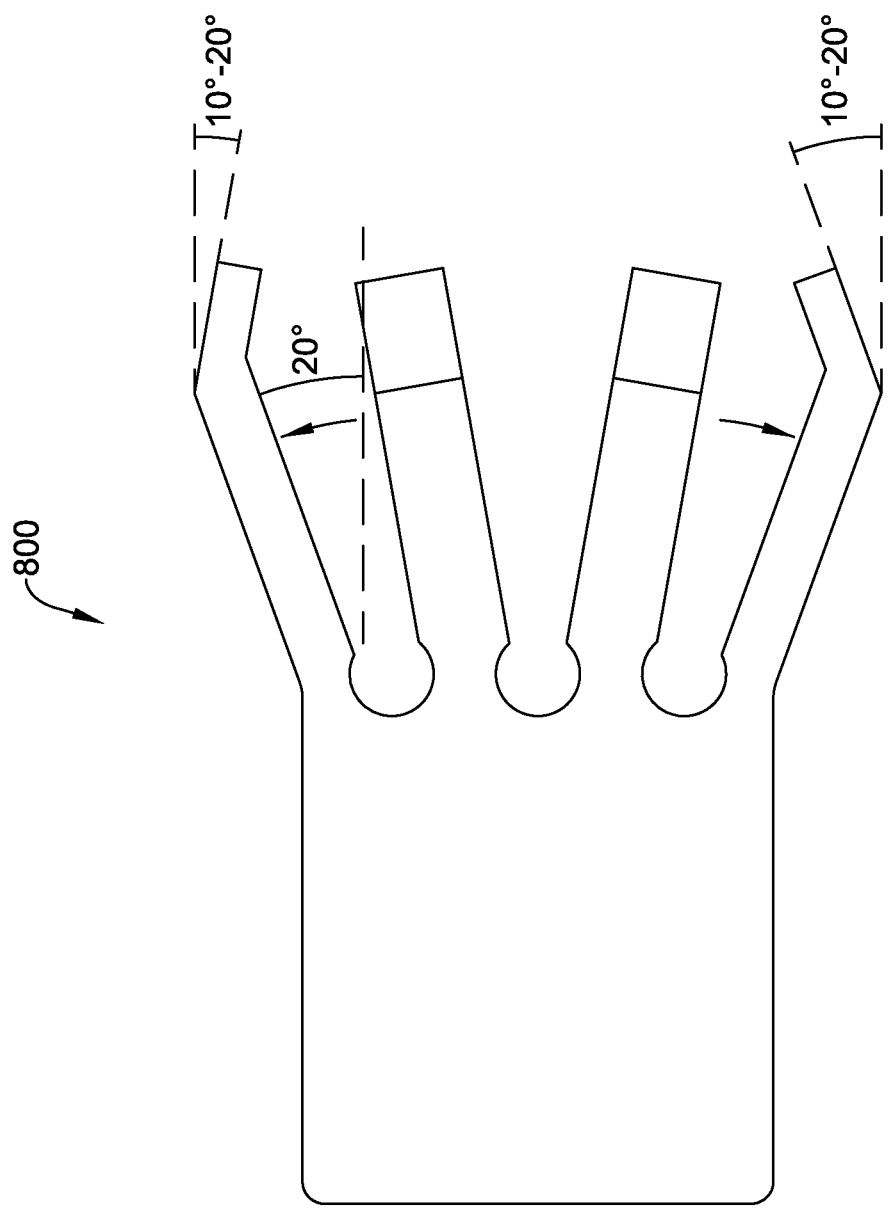
FIG. 8C shows an alternative version of the fifth example retention device in a deployed configuration.

FIG. 8A depicts an illustrative side-view of another example retention device 800 in a delivery configuration. FIG. 8B depicts an illustrative side-view of the example retention device 800 in a deployed configuration. FIG. 8C depicts an illustrative side-view of the example retention device 800 in another deployed configuration. The retention device 800 may be manufactured, configured, and operates similar to the retention device 700 and be implanted at similar locations within the patient. However, the retention device 800 is an example of a retention device that has more and narrower securing mechanisms.

Figure 9A:
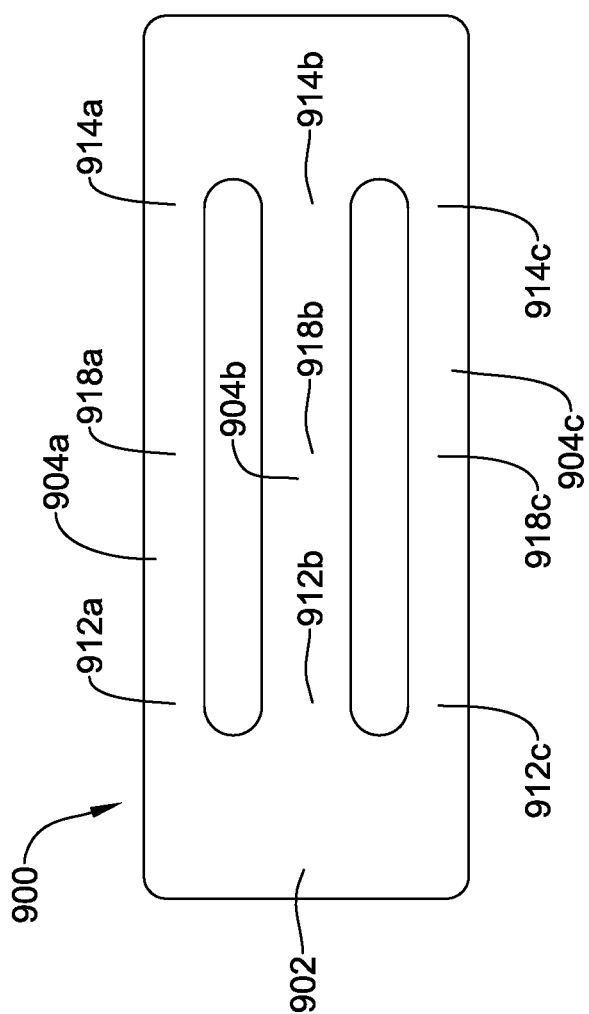
FIG. 9A shows a sixth example retention device in a delivery configuration.

FIG. 9A depicts an illustrative side-view of another example retention device 900 in a delivery configuration. The retention device 900 may be configured similar to the retention device 700, however, securing mechanisms 904A-904C of the retention device 900 may be cut and/or formed from a midsection 920 of an elongate body 902.

Figure 9B:
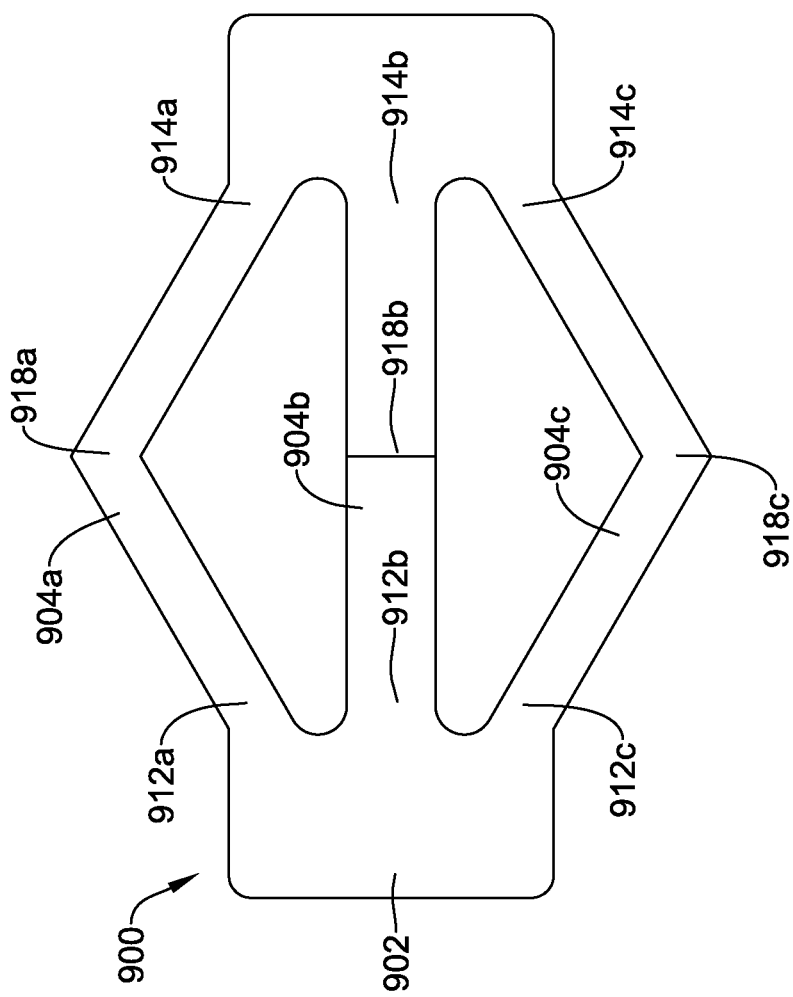
FIG. 9B shows the sixth example retention device in a deployed configuration.

FIG. 9B depicts an illustrative side-view of the example retention device 900 in a deployed configuration. In some cases, first ends 912A-912C of the securing mechanisms 904A-904C may bend or flex to extend intermediate sections 918A-918C to a first predefined angle relative to the elongate body and second ends 914A-914C of the securing mechanism 904A-904C may be configured to bend or flex to extend the intermediate sections 718A-718C to a second predefined angle, opposite the first predefined angle, relative to the elongate body 902. In some examples, the second predefined angle may be equal to the first predefined angle. However, this does not have to be the case. As shown in FIG. 9B, in this example, the first and second predefined angles may extend around about 10° to about 60° relative to the elongate body 902. In some cases, the first and second predefined angles may be 15°, 30°, 45°, 60°, etc. In some cases, the angles of separation may be substantially the same or equal across each of the securing mechanisms 904A-904C. In some cases, the angles of separation may not be the same or equal to one another. In some cases, since the first and second predefined angles may bend in the opposite directions, the intermediate sections 918A-918C may be configured to push against tissue of the patient when the retention device 900 is implanted in the patient.

In some examples such as that shown, the securing mechanisms 904A-904C may all have the same width, length and shape. Thus, while the examples shown generally have securing mechanisms 904A-904C that are symmetrically placed about the circumference of the retention device 900 with similar angular and shape characteristics, this need not be the case and different ones of the securing mechanisms 904A-904C may be differently oriented, sized or shaped, if desired. In addition, different ones of the securing mechanisms 904A-904C may have differing material properties, if desired. The various noted variations in shape, quantity, distribution, size, orientation, angular configuration, etc. may be incorporated in any of the following illustrative examples.

Figure 10:
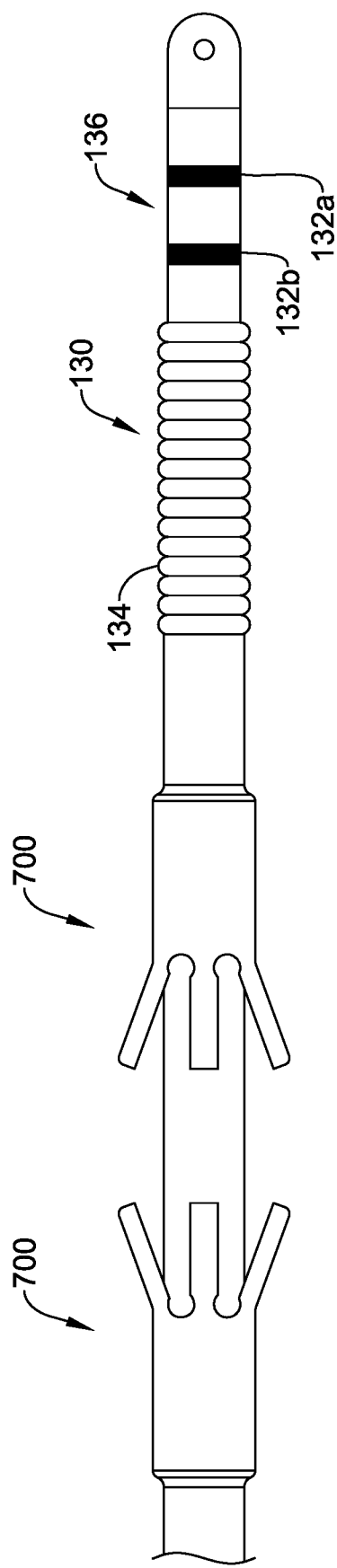
FIG. 10 shows the fourth example retention devices coupled to the lead.

FIG. 10 depicts the example retention device 700 coupled to the illustrative implantable lead 130. In some cases, as shown in FIG. 10, the retention device may be coupled to the implantable lead 130 by placing the implantable lead 130 through the hollow lumen 706 of the retention device 700 such that the retention device 700 substantially surrounds the lead 130. In some cases, a sheath may be disposed over the retention device 300 prior to or during implantation.

Various implantation techniques may be used with the anchoring systems are shown above. Two examples for implantation of a subcutaneous-only defibrillator follow; other implementations are contemplated as well. For example, an anchoring device as shown above may be used to secure a single or multiple coil subcutaneous lead electrode for use with a transveous or epicardial cardiac therapy device. An anchoring device as shown above may be used to secure a lead for use with a spinal cord stimulation device. An anchoring device as shown may be used to secure a lead near the implantable pulse generator (or on the neck) of a patient having a deep brain stimulation device. An anchoring device as shown may also be used to secure a lead for use in other neural or cardiac stimulus or therapy devices, without limitation.

Figure 11A:
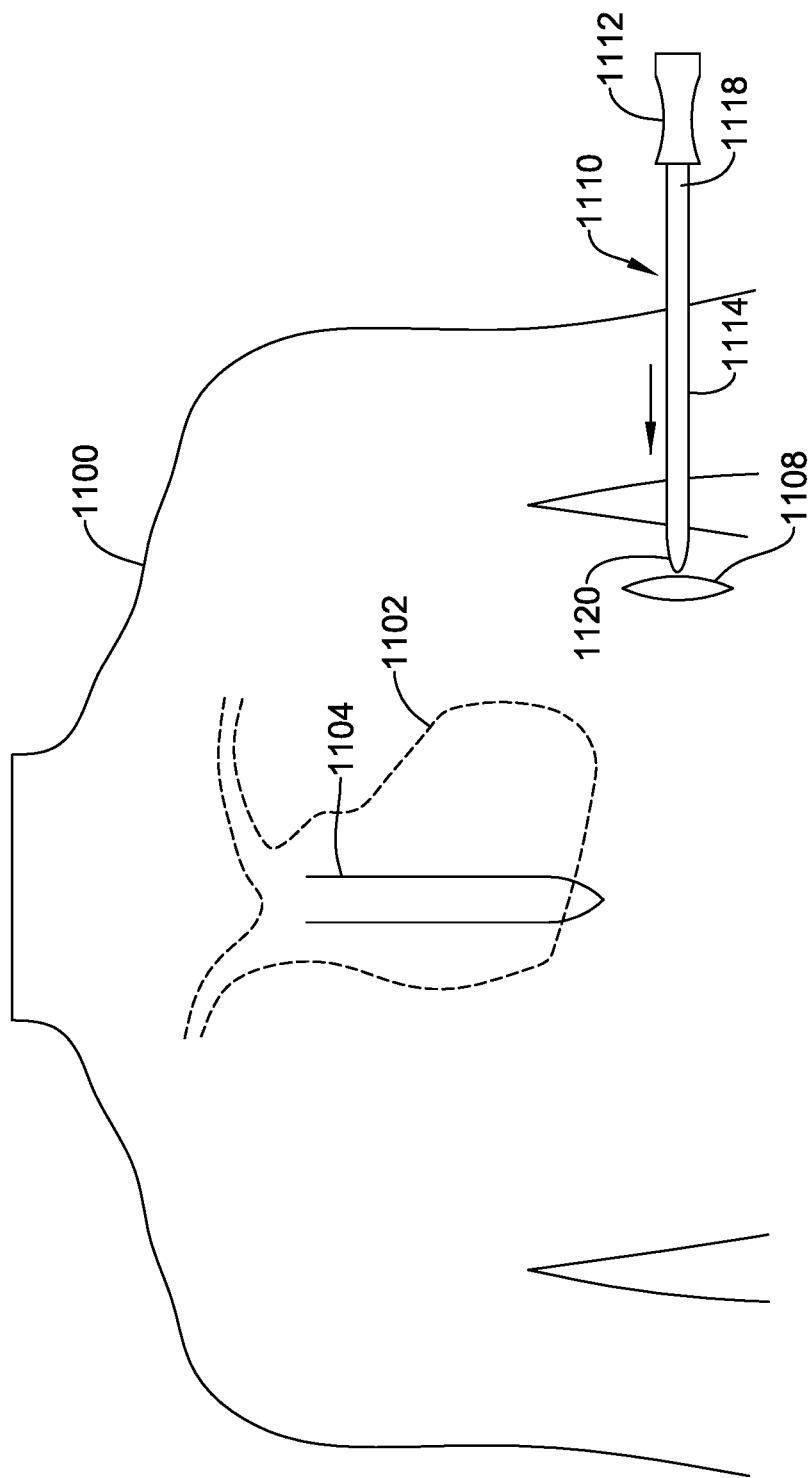
FIGS. 11A-11C illustrate a first method for implanting an implantable medical device.
Figure 11B:
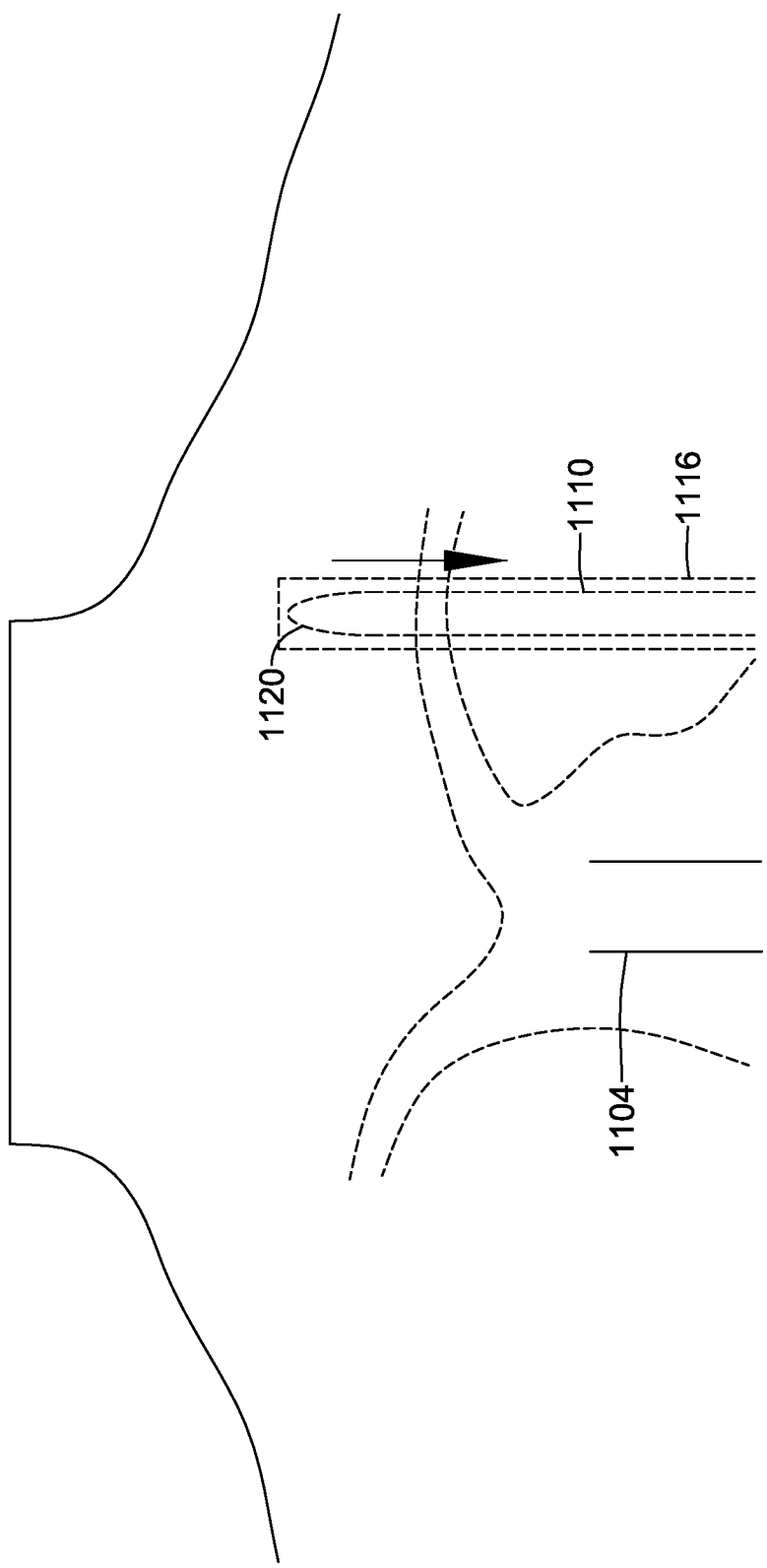
Figure 11C:
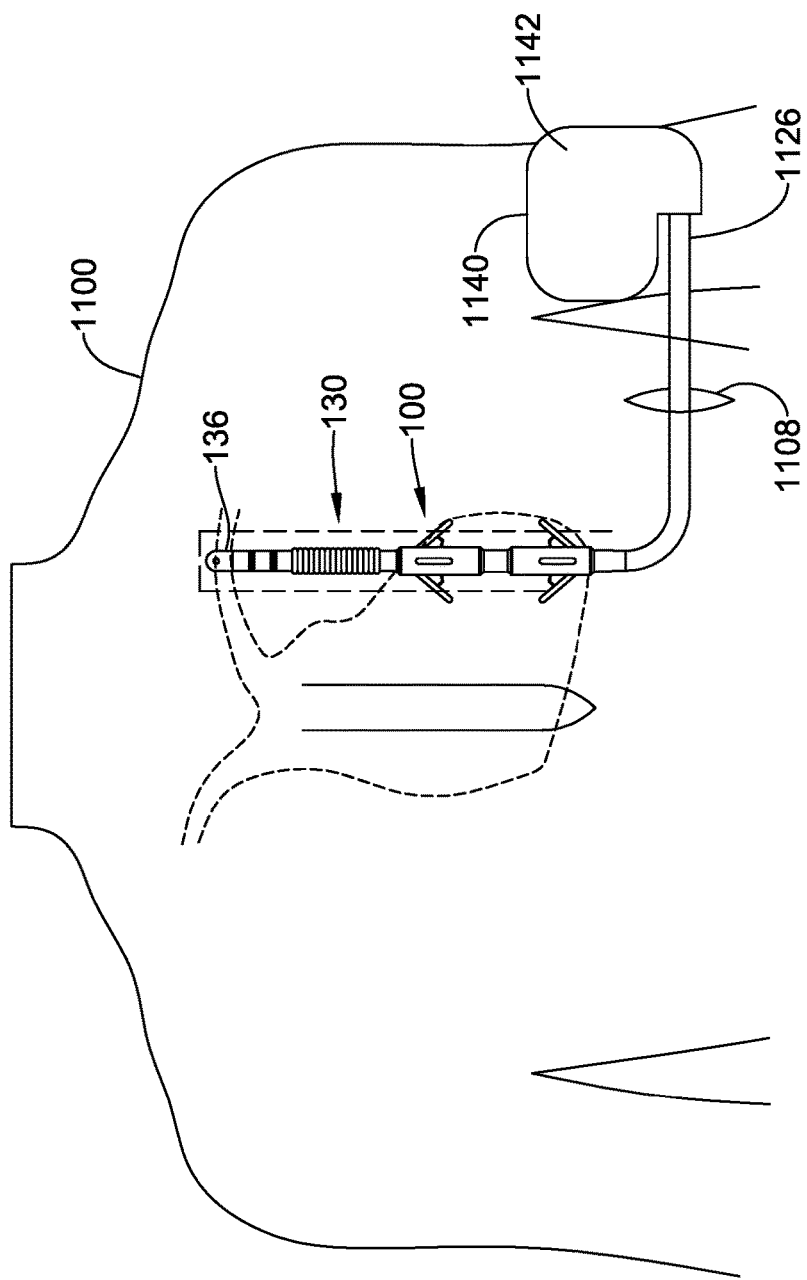

FIGS. 11A-11C depict an illustrative one incision method of implanting an implantable medical device (IMD) in a patient 1100. In some cases, the implantable lead 130, having the retention device 100 disposed thereon, may be used. Beginning with FIG. 11A, certain anatomy of the patient 1100 is highlighted including a heart 1102 and sternum 1104. An axillary incision may be made near the left axilla of the patient 1100, as shown at 1108. An insertion tool 1110 may be used in the procedure. The insertion tool 1110 may have a handle 1112 at a proximal end 1118, and an elongate shaft 1114 extends distally from the handle 1112 toward a distal dissecting tip 1120. The distal tip 1120 may be shaped for dissection of subcutaneous tissue. In one example, the distal tip 1120 has a tapered blunt tip, allowing for passage by dissection through subcutaneous tissue without encouraging piercing through the epidermis.

A channel(s) may optionally be provided in the insertion tool 1110 to allow infusion of fluids for antiseptic, anti-inflammatory, pain reduction, or other purposes at the dissecting tip or along the length thereof. If ingrowth or adhesion is desired, a tissue adhesive or steroid may be infused.

As shown by the arrow in FIG. 11A, the insertion tool 1110 may be inserted through the axillary incision 1108. In some cases, the insertion tool 1110 may be deflectable or steerable and may be used to create a tunnel 1116 from the axillary incision 1108, just to the left of and superior of the xiphoid near the lower portion of the sternum 1104, and advanced generally parallel to the sternum 1104, as shown in FIG. 11B. In an example, the insertion tool 1110 is advanced as shown with an introducer sheath thereon. The insertion tool 1110 may then be withdrawn, keeping the introducer sheath in place.

In some cases, the lead 130 may be prepared for use by applying the retention device 100 thereon at a desired location such as by sliding the retention device 100 over the proximal or distal end of the lead 130. Alternatively, the lead 130 may be provided by the manufacturer with the retention device 100 pre-attached and bonded to the lead 130, such as by using an adhesive, welding, heating, shrinking, or co-manufacturing process such as insert molding. The retention device 100 may include a longitudinal slit to allow lateral placement onto a lead, if desired. In some examples, a sheath may be placed over the lead 130 and retention device 100 to aid in holding the retention device 100 at the desired location on the lead, and to hold the securing mechanisms of the retention device in a delivery configuration, preventing them from engaging tissue during implantation prior to reaching a desired implant position.

As shown in FIG. 11C, the lead 130 may be positioned at a desired location in the tunnel 1116 by insertion through the introducer sheath. Removal of the introducer sheath and the sheath placed over the lead 130 (if one is used) then allows the retention device 100 to become engaged to the patient tissue at a desired location, such as near the xiphoid of the patient, as the securing mechanisms on the retention device 100 expand from the delivery configuration to a deployed configuration. At the end of this step or prior to this step, a proximal plug 1126 of the lead 130 may be located relatively near the axillary incision 1108, though this may depend on the anatomy of the patient 1100 and the length of the lead 130. In some cases, the proximal plug or connector 1126 of the lead 130 may be attached to an implantable canister 1140. In some cases, the lead 130 coupled to the canister may comprise the IMD.

The canister 1140 may include a housing 1142 to house operational circuitry. For a cardiac electrical stimulus device, the operational circuitry may couple to the electrodes on the lead via conductors and be configured to analyze biological signals and deliver output therapy in the form of at least one of bradycardia pacing, anti-tachycardia pacing, cardiac resynchronization therapy, or defibrillation, using the electrodes on the lead 130. In other examples, non-cardiac therapy and/or stimulus may be provided such as by having a drug infusion pump as the canister 1140 for infusing a drug or other substance for example for diabetes or pain management, and/or by having a neuromodulation or neurostimulation device adapted to deliver electrical stimuli to a desired body part to induce, modulate, or block signals and/or activities; for example, spinal cord stimulation may be applied to alleviate or block pain, vagus nerve and/or deep brain stimulation may be applied to address various conditions.

In the example shown, the canister 1140 may then be implanted through the axillary incision 1108 and sutured to the patient's 1100 tissue. If desired, in addition to or as an alternative to suturing the canister 1140 once positioned, a suture sleeve or retention device as shown herein may be provided in the axillary pocket to isolate the lead from canister motion. Having the IMD (including the lead 130) implanted with the retention device 100 may provide several potential benefits. For instance, the retention device 100 may improve stability during implantation of the lead 130. The retention device 100 may also improve stability during acute implant duration, prior to tissue ingrowth. In some cases, the retention device 100 may potentially improve long term stability, including a chance for less noise due to electrode movement and reduced inappropriate shocking. In some cases, the retention device 100 may eliminate the need for suturing the lead down to the patient fascia. That is, a physician may implant the device without suturing the retention device 100 to the patient, instead relying on the securing mechanisms thereof to hold it in place and thus reducing the time needed for implantation.

Several modifications may be made to the method of implanting the IMD described in FIGS. 11A-11C. For example, rather than the steps of FIGS. 11A-11C to place the lead 130 over the ribs and alongside the sternum, a substernal approach may be taken by advancing the lead beneath the ribs. The lead may be directed to an entirely different location, such as near the spine, kidney, or elsewhere. The canister 1140 may be placed elsewhere as well, such as in the abdomen, near or in the buttocks, or adjacent or near the clavicle, or any other desired position.

In some cases, several alternative structures for leads and retention devices may be used and additional steps/features may be are provided. In some examples, the retention device may take the form of the retention devices 100, 300, 500, 700, 800, or 900. For instance, in the case where the retention device 900 is used, the steps of positioning the lead at a desired location in the tunnel 1116 and removing of the sheath placed over the lead 130 during implant may be similar to the steps described above. The securing mechanisms can then move to their deployed configuration.

FIGS. 12A-12E depict an illustrative two incision method of implanting an IMD in the patient 1100. Similar to the one incision method shown in FIGS. 11A-11C, the implantable lead 130, having the retention device 100 disposed thereon, may be used. Beginning with FIG. 12A, a xiphoid incision 1206 may be made just to the left of and superior of the xiphoid near the lower portion of the sternum 1104, and an axillary incision may be made near the left axilla of the patient 1100, as shown at 1108. An insertion tool 1210 may be used in the procedure. The insertion tool 1210 may have a handle 1212 at a proximal end 1218, and an elongate shaft 1214 extends distally from the handle 1212 toward a distal dissecting tip 1220 that includes an attachment feature 1216. The attachment feature 1216 is shown as a suture opening, however, other suitable attachment features known in the art may be used. The distal tip 1220 may be shaped for dissection of subcutaneous tissue. In one example, the distal tip 1220 has a tapered blunt tip, allowing for passage by dissection through subcutaneous tissue without encouraging piercing through the epidermis. A channel(s) may be provided in the insertion tool 1210 to allow infusion of fluids for antiseptic, anti-inflammatory, pain reduction, or other purposes at the dissecting tip or along the length thereof. If ingrowth or adhesion is desired, a tissue adhesive or steroid may be infused as well. As shown by the arrow in FIG. 11A, the insertion tool 1210 may be inserted through the xiphoid incision 1206 and advanced toward the axillary incision 1108.

Figure 12A:
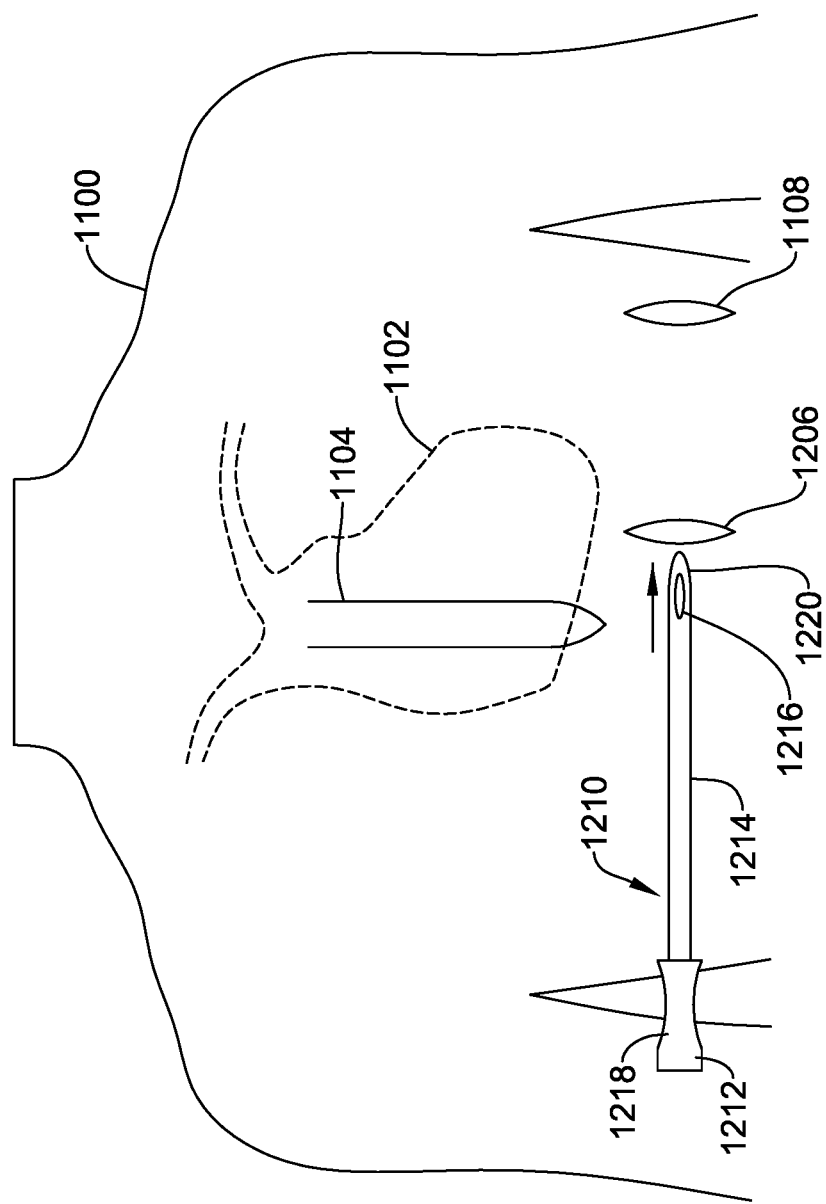
FIGS. 12A-12E illustrate a second method for implanting the implantable medical device.
Figure 12B:
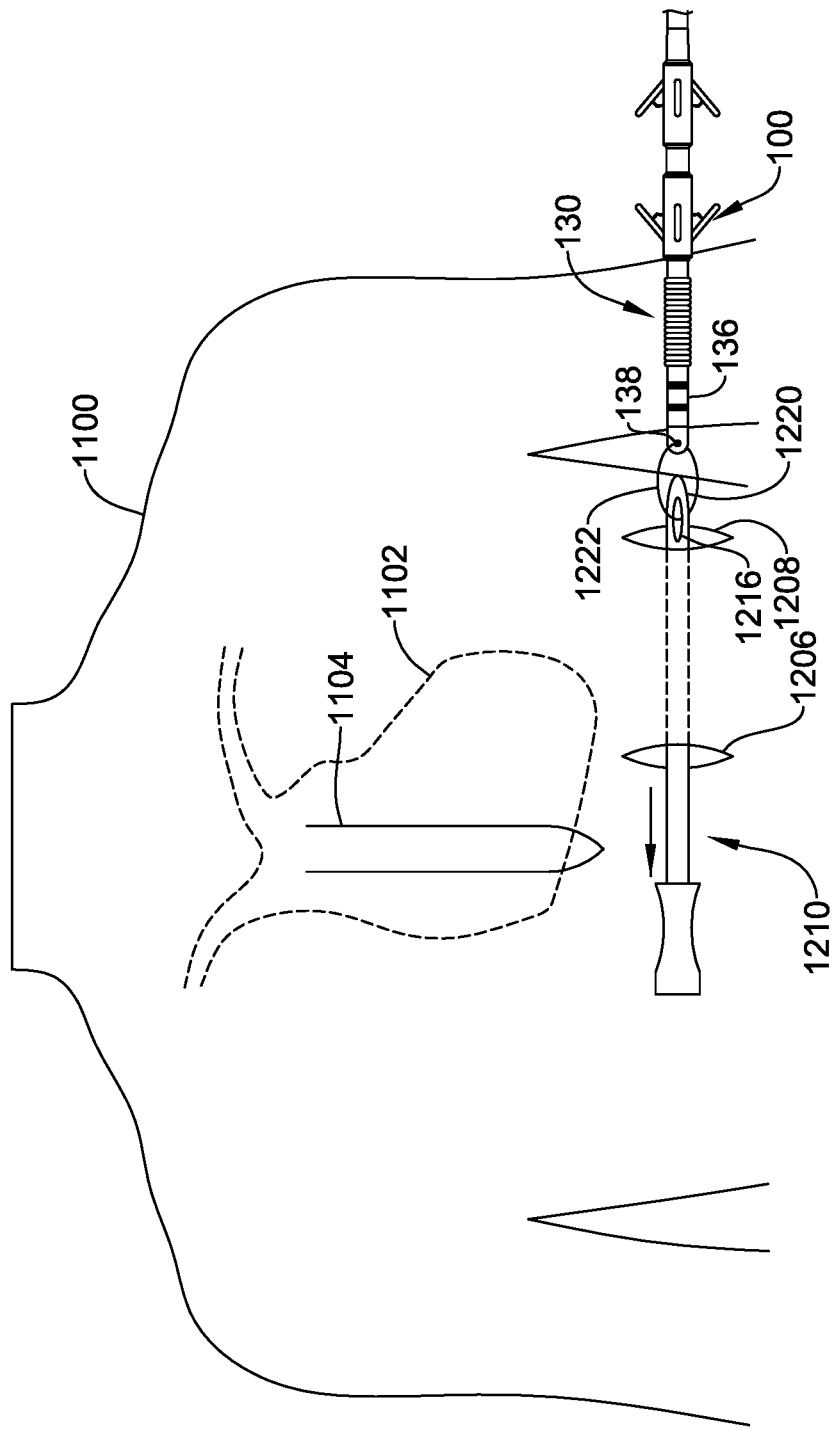

As shown in FIG. 12B, the lead 130 may be prepared similar to the description above in regard to FIGS. 11A-11C. In some cases, the insertion tool 1210 may be inserted into the xiphoid incision 1206 until its distal tip 1220, including the attachment feature 1216, can be accessed through the axillary incision 1108. Then the suture 1222 may be used to attach the attachment feature 1216 of the insertion tool 1210 to an attachment feature 138 on a distal tip portion 136 of the lead 130. If needed, the lead 130 may be prepared by attaching a retention device 100 (before or after attachment to the insertion tool 1210). Alternatively, the retention device 100 may be permanently attached to the lead 130 during manufacturing thereof.

Figure 12C:
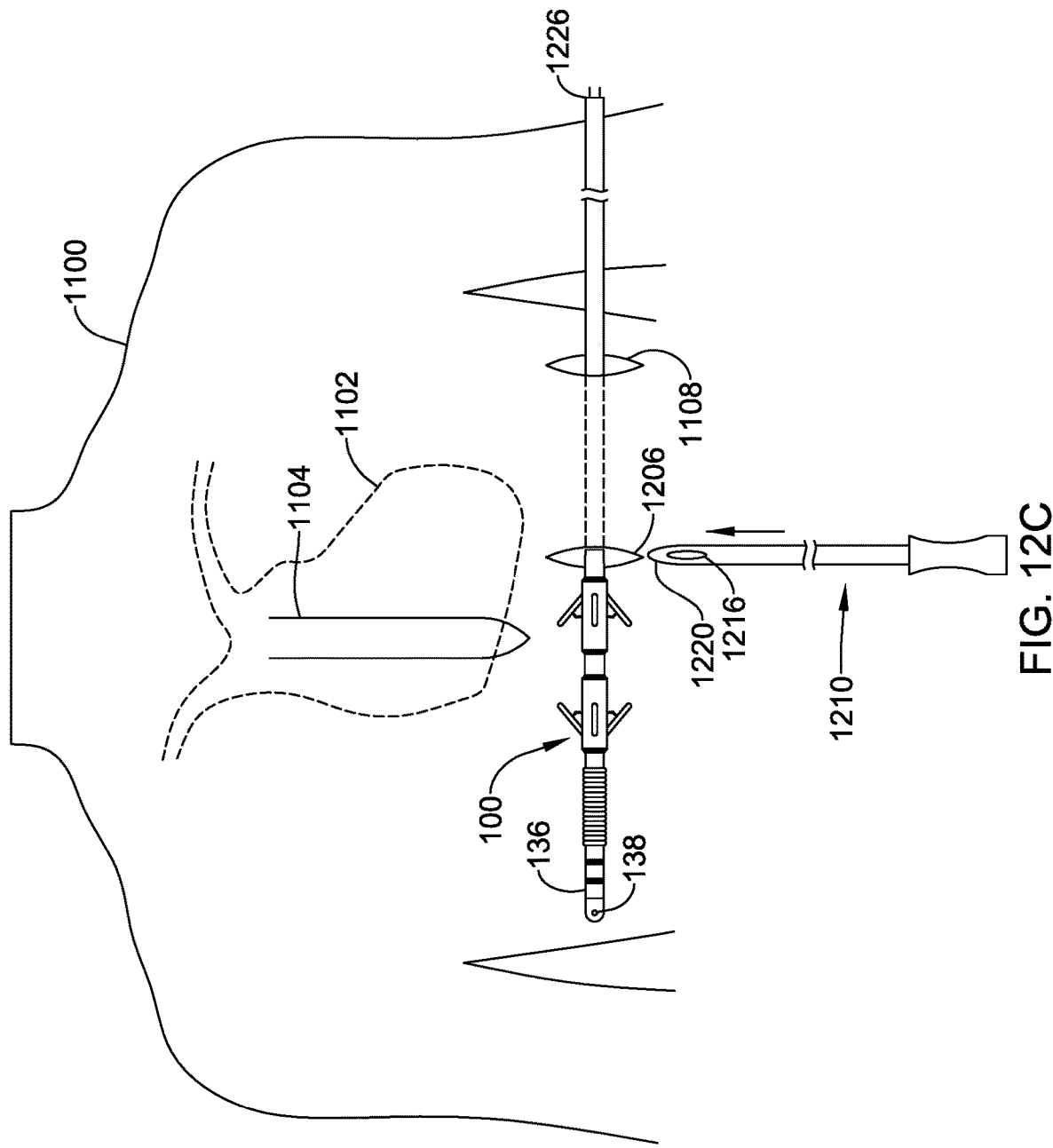

In some examples, a sheath may be placed on the lead, either at the time of surgery or as a preloaded system, to prevent the retention device 100 engaging tissue during its introduction into the patient. Next, the insertion tool 1210 may be withdrawn through the xiphoid incision 1206, with the suture 1222 pulling the lead 130 into the patient's subcutaneous tissue through the axillary incision 1108. Alternatively, a sheath may be used to advance the lead 130 into tissue without the use of the suture to pull the lead 130. The end of this pulling step is shown in FIG. 12C, where the attachment feature 138 at the distal tip portion 136 of the lead 130 extends through the xiphoid incision 1206 and forceps (not shown) may be used to grasp the suture 1222, which may be cut from the attachment feature 1216. At the end of this step, the proximal plug 1226 of the lead 130 may be located relatively near the axillary incision 1108.

If used, a sheath may be removed after the lead has been pulled to and through the axillary incision. Alternatively, the sheath may be kept in place until implantation is complete. In still other alternatives, no sheath is used during this tunneling and pulling step. For example, no sheath may be needed during pulling from the axillary incision to the xiphoid incision if the securing mechanisms are biased to allow passage through tissue in one direction but not the other.

Figure 12D:
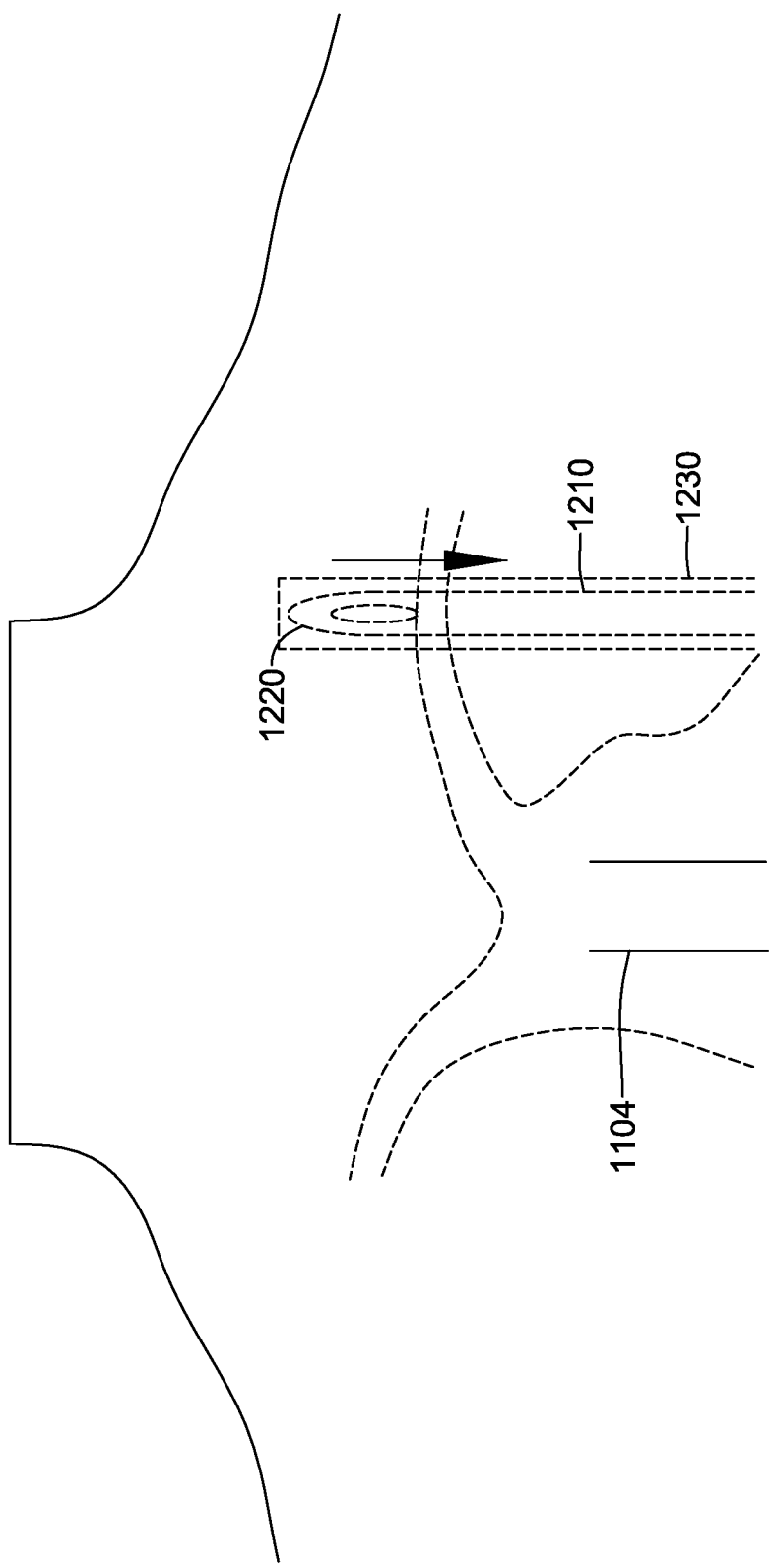
Figure 12E:
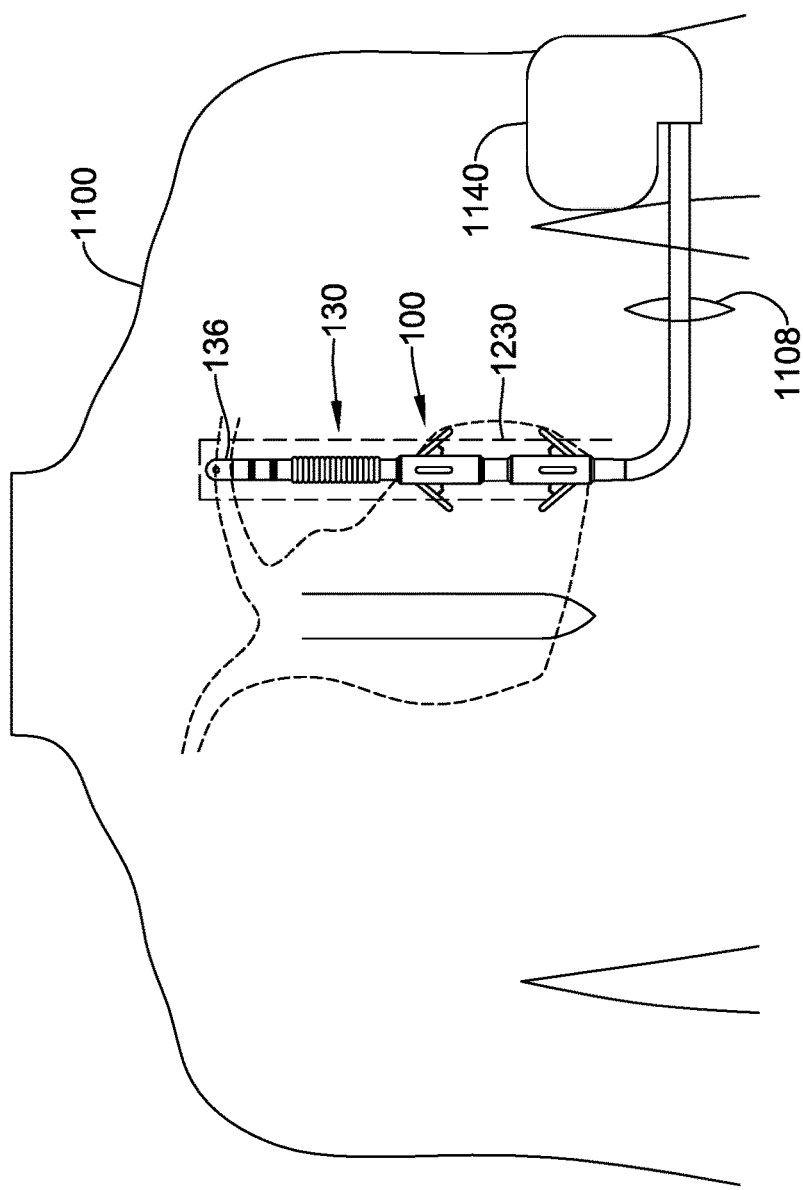

In the example shown in FIG. 12C and as described herein, the distal tip 1220 of the insertion tool 1210 may be shaped to allow for passage by dissection through subcutaneous tissue. Accordingly, the insertion tool 1210 may be reinserted into the xiphoid incision 1206 and advanced generally parallel to the sternum 1104 to create a tunnel 1230, as shown in FIG. 12D. Though not shown, an introducer sheath may be placed over the insertion tool 1210 during the step shown in FIGS. 12C-12D. The insertion tool 1210 may then be withdrawn, with the introducer sheath left in place. As shown in FIG. 12E, the lead 130 may be reinserted into the xiphoid incision 1206 and advanced generally through the tunnel 1230 and retained introducer sheath. The introducer sheath is then split and removed over the lead. Removal of the introducer sheath allows the retention device 100 to engage the patient tissue at a desired location, such as near the xiphoid of the patient, as the securing mechanisms on the retention device 100 expand from the delivery configuration to the deployed configuration.

In some examples, if the introducer sheath is used in both passage through the axillary-xiphoid tunnel and in the parasternal tunnel, it would be removed at the left axilla. If the introducer sheath is used only in the parasternal tunnel, or is removed after the passage from axilla to xiphoid and a second introducer sheath used for the parasternal tunnel, then the introducer sheath would be removed at the xiphoid. The proximal plug 1226 of the lead 130 may then be attached to the canister 1140 and the canister 1140 may be implanted through the axillary incision 1108 and sutured to the patient's 1100 tissue.

In some examples, a two incision, two sheath approach may be used similar to that shown in U.S. Provisional Patent Application Ser. No. 62/576,910. For example, a first tunnel from the axillary incision to the xiphoid may be formed using a first insertion tool with a first sheath thereon, with the first insertion tool then removed to leave the first sheath in place in the axillary-xiphoid tunnel. A second tunnel from the xiphoid incision to a desired position, such as near the manubrium, may be formed using a second insertion tool lead having a second sheath thereon, with the second insertion tool then removed to leave the second sheath in place. The lead, having an anchoring or retention apparatus as shown herein attached or integral thereto may be advanced into first and second sheaths in any order or direction, as desired. For example, the proximal end of the lead may be passed through the first sheath from the xiphoid to the axilla, while the distal end of the sheath is then (or already has been) advance into the second sheath; once a desired position is achieved, both sheaths are removed to allow the lead to become anchored in place. In another example, the distal end of the lead is passed through the first sheath from the axilla to the xiphoid, and then into the second sheath from the axilla to a desired location; once a desired position is achieved, both sheaths are removed to allow the lead to become anchored in place. For such examples, the lead is passed through a subcutaneous tunnel by inserting a portion thereof into and through a sheath that has already been placed.

If desired, a three incision technique for subcutaneous defibrillator implantation may be used that may be generally similar, except with respect to the use of the retention device, to certain examples in U.S. Pat. No. 7,655,014, titled APPARATUS AND METHOD FOR SUBCUTANEOUS ELECTRODE INSERTION, the disclosure of which is incorporated herein by reference. Here, for example, the time spent suturing at the xiphoid incision may be reduced by using a retention device as shown herein at that location; alternatively or additionally a retention device as shown herein may be used at the third incision—superior alongside the sternum.

In the various examples, shown, the end location for the retention device 100 may be in several different spots. In some examples, the retention device 100 will be placed at the distal end of the lead and will engage tissue more or less near the sternum superior to one or more electrodes of the lead 130. In other examples, the retention device 100 will end up near the xiphoid process, inferior to the anatomical position of the electrodes on the lead 130. In other examples, the retention device 100 may be positioned along the inframammary crease.

At a high level, a single incision method may omit each of the xiphoid and sternal incisions; a sheath is used to secure the parasternal tunnel and may additionally serve to support lead passage and/or to restrain or retain securing mechanisms on the lead. The present invention, for the single incision method, aids omission of at least the xiphoid incision by providing anchoring at a desired location on the lead. The single incision method may use a curved, telescoping and/or deflecting or steerable tunneling system, such as in U.S. Pat. No. 10,617,402, titled MINIMALLY INVASIVE METHOD TO IMPLANT A SUBCUTANEOUS ELECTRODE, the disclosure of which is incorporated herein by reference. A single incision method may also or instead use a method as shown in US PG Pat. Pub. No. 20190054302, titled SINGLE INCISION SUBCUTANEOUS IMPLANTABLE DEFIBRILLATION SYSTEM, the disclosure of which is incorporated herein by reference.

As illustrated in these examples, the present invention facilitates flexibility in selection of the implant procedure. For example, with a very active or young patient where lead migration is a great concern, or for a patient with a lot of adipose tissue that may make lead anchoring more challenging, a multiple incision technique may be performed using the retention devices to hold the lead in place by multiple approaches. For other patients, a single incision technique may be used relying solely on the retention device, or a two-incision technique that omits a xiphoid incision relying on a retention device at an intermediate fixation point as well as, optionally, distal tip fixation by a retention device. Such flexibility may allow the physician to make changes to the planned procedure intraoperatively, without having to discard a lead that is deemed unsuitable to the particular patient. A physician may determine, through gentle tugging at the proximal (or distal) end of the lead, whether additional retention devices need to be applied.

Figure 13:
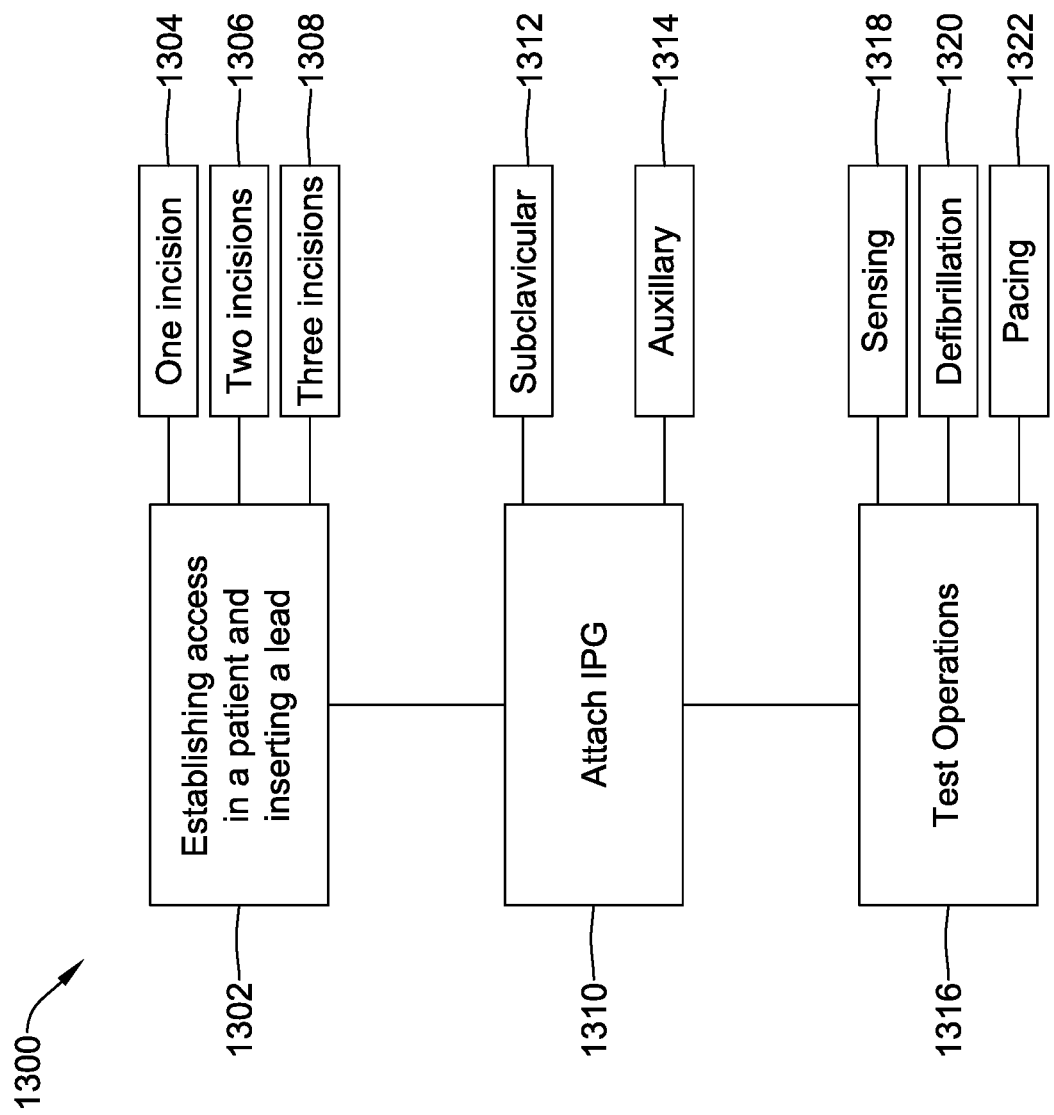
FIG. 13 is a block flow diagram for an illustrative method.

FIG. 13 is a block flow diagram of an illustrative method 1300 for providing an IMD system to a patient. As shown, the method 1300 comprises establishing access in a patient and inserting a lead 1302, attaching an implantable pulse generator (IPG) to the lead 1310, and performing test operations 1316. The IPG may also be referred to herein as a canister or implantable canister.

For example, establishing access to the patient and inserting a lead 1302 may include using a one incision implantation method, such as described above relative to FIGS. 11A-11C as indicated at 1304. In another example, establishing access to the patient and inserting a lead 1302 may include using a two-incision implantation method 1306, generally as shown above relative to FIGS. 12A-12E. In another example, a three-incision implantation method may be used to establish access to the patient.

Regardless of the incision method used, once the lead is at a selected position or configuration in the patient, securing mechanisms located on a retention device of the lead may engage, push against, and/or anchor the lead to the patient tissue, such as near the xiphoid of the patient. Suturing to the fascia may thus be reduced or omitted.

In an example, attaching an IPG to the lead 1310 may include attaching to a canister located in a subclavicular location 1312, historically a common place to put an implanted canister for a transvenous defibrillator or pacemaker. In another example, attaching to an IPG may include attaching to a canister located in an axillary position 1314, such as that used with the S-ICD System. Other IPG locations may be used. Attachment may be directly to the IPG or to a splitter, yoke, or lead extension, if desired.

In an example, test operations 1316 may be used to verify one or both of device functionality and efficacy. For example, sensing operations 1318 may be tested and configured to check for adequate signal availability, for example, or by setting gain, filtering, or sensing vector selection parameters. Defibrillation operations 1320 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 1320 may include determining for a given patient an appropriate defibrillation threshold, and setting a parameter for therapy delivery at some safety margin above the defibrillation threshold. For other, non-cardiac-electrical systems, (such as a drug pump or neuromodulation system), other therapy testing methods may be applied, as is conventional for those other products.

In an example, pacing testing operation 1322 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

As noted above, the illustrative retention devices may be formed of any biocompatible material. Some examples include elastic, biocompatible alloys capable of forming stress induced martensite (SIM). Nitinol (TiNi) is an example of such materials. A retention device may be formed from stainless steel, such as high tensile stainless steel, or other materials, including metals and metal alloys, such as tungsten, gold, titanium, silver, copper, platinum, palladium, iridium, ELGILOY nickel-cobalt alloys, cobalt chrome alloys, molybdenum tungsten alloys, tantalum alloys, titanium alloys, etc. A retention device may be formed from a lubricious polymer, such as a fluorocarbon (e.g., polytetrafluoroethylene (PTFE)), a polyamide (e.g., nylon), a polyolefin, a polyimide, or the like). A retention device may be formed of polyethylene, polyvinyl chloride (PVC), ethyl vinyl acetate (EVA), polyethylene terephthalate (PET), and their mixtures and copolymers. Another useful class of polymers is thermoplastic elastomers, including those containing polyesters as components. A retention device may also be comprised of such materials as soft thermoplastic material, polyurethanes, silicone rubbers, nylons, polyethylenes, fluorinated hydrocarbon polymers, and the like. A retention device may also be of a member selected from a more flexible material such as low density polyethylene (LDPE), polyvinylchloride, THV, etc. Still in further embodiments, a retention device may be composed of a combination of several these materials. In certain embodiments, a retention device may be formed of, impregnated with, or comprise a maker made of a radiopaque material such as, for example and without limitation barium sulfate (BaSO4), bismuth trioxide (Bi2O3), bismuth subcarbonate (Bi2O2CO3), bismuth oxychloride (BiOCl), and tungsten.

Retention devices may be formed by molding, such as injection molding, or insert molding. In some examples, different parts or layers may be included such as by, for example, extruding a core tube having one or a plurality of layers (such as a lubricious inner layer with a tie layer thereon to allow ready attachment of additional material) of the retention device and insert molding an outer surface thereon of a different material, with the securing mechanisms added via the insert molding process. In another example, a wire member may be used as a starting point for an insert molding process, wherein the wire member comprises a set of tines to use as securing mechanisms on which a polymeric material is added.

Lead structures for use with the present invention may take any suitable type and use any suitable material, such as the materials noted above. Internal longitudinal or lateral support members, such as braids, core wires, etc. may be provided. Extrusion or molding may be used for lead manufacture. Internal conductors in the lead may be formed of any suitable material (stainless steel, titanium, gold, silver, or any other conductive material may be used) and may take any suitable form, such as simple wires, coated wires, braided or wound wires, drawn wires, and/or drawn filled tubes, or other structures. The lead may include on all or a portion thereof various coatings such as an anti-microbial coating to reduce the likelihood, severity, and/or progression of infection.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems. The present invention may be used for non-cardiac devices such as, for example and without limitation, the Precision Novi and Precision Spectra neuromodulation devices offered by Boston Scientific. Any suitable lead structure may be used, such as leads adapted for subcutaneous implantation for cardiac monitoring or therapy purposes, and/or leads adapted for use in spinal, deep brain, or peripheral neuromodulation systems such as vagus or sacral nerve therapies. When used in a neuromodulation system, the methods of FIG. 13 may be modified to swap out the test operations at 1316 to determining appropriate therapy settings using methods well known in the neuromodulation field. The present invention may also be used in association with a drug pump that injects a fluid; rather than anchoring an electrical lead, a fluid injection catheter used by the drug pump may be implanted and anchored in place.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A retention device for use with an implantable medical device (IMD) having a lead, the lead having a proximal end for coupling to a canister and a distal end, the retention device comprising:
   an elongate body in the form of a continuous tube having an open proximal end, an open distal end, and a hollow lumen extending from the proximal end to the distal end configured to receive the lead; and
   a first securing mechanism defining a delivery configuration in which the first securing mechanism is collapsed toward the elongate body, and a deployed configuration in which the first securing mechanism extends outward from the elongate body, having:
      a first end coupled to the elongate body;
      a second end opposite the first end and configured to push against tissue of a patient in the deployed configuration; and
      an intermediate portion extending between the first and second ends; and
   a first linking element having a first end coupled to the elongate body and a second end coupled to the intermediate portion of the first securing mechanism, wherein the one or more first linking elements limit radial extension of the securing mechanism in the deployed configuration;
   wherein the elongate body defines a distance between the first end of the first securing mechanism and the first end of the first linking element and the distance does not change between the delivery configuration and the deployed configuration.

2. The retention device of claim 1 further comprising:
   a second securing mechanism defining a delivery configuration in which the second securing mechanism is collapsed toward the elongate body, and a deployed configuration in which the second securing mechanism extends outward from the elongate body, having:
      a first end coupled to the elongate body;
      a second end opposite the first end and configured to push against tissue of a patient in the deployed configuration; and
      an intermediate portion extending between the first and second ends; and
   a second linking element having a first end coupled to the first securing mechanism and a second end coupled to the second securing mechanism.

3. The retention device of claim 2 wherein the first and second securing mechanisms are circumferentially spaced about the elongate body.

4. The retention device of claim 1, wherein the first linking element is configured to prevent prolapse of the first securing mechanism in the deployed configuration.

5. The retention device of claim 1 wherein the first linking element limits extension of the first securing mechanism to an angle in the range of about 10 to about 60 degrees, relative to the elongate body.

6. The retention device of claim 1 wherein the retention device comprises silicone.

7. The retention device of claim 1 wherein the first securing mechanism comprises a nitinol wire having a transition temperature, the nitinol configured to assume a deployed configuration shape above the transition temperature thereof to anchor in tissue.

8. An implantable medical device system comprising:
   an implantable canister housing operational circuitry for one or more of monitoring a body function and delivering a therapy output;
   a lead configured for implantation in the body and having at least a first end configured for coupling to the implantable pulse generator; and
   the retention device of claim 1, wherein the lead is sized and shaped to be received in the lumen of the retention device.

9. A retention device for use with an implantable medical device (IMD), the retention device comprising an elongate body having a proximal end, a distal end, a hollow lumen extending from the proximal end to the distal end configured to receive a lead of the IMD, the retention device further comprising one or more securing mechanisms having a first end configured to bend such that a portion of the one or more securing mechanisms extends to a predefined angle relative to the elongate body;
   wherein the one or more securing mechanisms includes a second end that is configured to extend to the predefined angle and push against tissue of a patient; and
   wherein the elongate body is formed from a tube with the securing mechanisms formed from a cut portion of the tube.

10. The retention device of claim 9 wherein the cut portion of the tube is located between the proximal and distal ends thereof.

11. The retention device of claim 9 wherein the cut portion of the tube is located at an end thereof and includes plurality of cuts extending from the end towards a middle of the tube with the one or more securing mechanisms defined between adjacent cuts.

12. The retention device claim 9 wherein the one or more securing mechanisms comprise nitinol, the nitinol adapted to assume a shape above the transition temperature thereof that facilitates anchoring in tissue.

13. A method of implanting an implantable lead having a first end for coupling to an implantable medical device and a second end for implantation at a target site in the patient, with a lead body extending therebetween, the method comprising the use of a retention device having a first securing mechanism for securing the retention mechanism at a desired location in tissue, the method comprising:
  inserting the implantable lead into the patient with the retention device placed on the lead at a desired location thereon and with a sheath disposed about at least a portion of the lead and compressing the first securing mechanism of the retention device in a delivery configuration; and
  at least partly withdrawing the sheath to a position proximal of the first securing mechanism, wherein the first securing mechanism responds to withdrawal of the sheath by self-expanding to a deployed configuration to anchor the implantable lead to tissue of the patient; wherein the retention device comprises:
  an elongate body in the form of a continuous tube having an open proximal end, an open distal end, and a hollow lumen extending from the proximal end to the distal end configured to receive the lead; and
  the first securing mechanism, defining a delivery configuration in which the first securing mechanism is collapsed toward the elongate body, and a deployed configuration in which the first securing mechanism extends outward from the elongate body, having:
    a first end coupled to the elongate body;
    a second end opposite the first end and configured to push against tissue of a patient in the deployed configuration; and
    an intermediate portion extending between the first and second ends; and
  a first linking element having a first end coupled to the elongate body and a second end coupled to the intermediate portion of the first securing mechanism, wherein the one or more first linking elements limit radial extension of the securing mechanism in the deployed configuration;
  wherein the elongate body defines a distance between the first end of the first securing mechanism and the first end of the first linking element and the distance does not change as the first securing mechanism moves from the delivery configuration to the deployed configuration.

14. The method of claim 13, wherein the retention device further comprises:
  a second securing mechanism circumferentially spaced from the first securing mechanism and defining a delivery configuration in which the second securing mechanism is collapsed toward the elongate body, and a deployed configuration in which the second securing mechanism extends outward from the elongate body, having:
    a first end coupled to the elongate body;
    a second end opposite the first end and configured to push against tissue of a patient in the deployed configuration; and
    an intermediate portion extending between the first and second ends; and
  a second linking element having a first end coupled to the first securing mechanism and a second end coupled to the second securing mechanism.

15. The method of claim 13 wherein the first linking element is configured to prevent prolapse of the first securing mechanism in the deployed configuration, thereby limiting movement of the first securing mechanism when the sheath is withdrawn to an angle in the range of about 10 to about 60 degrees, relative to the elongate body.

16. The method of claim 13 wherein the retention device comprises silicone.

17. The method of claim 13 wherein the first securing mechanism comprises a nitinol wire having a transition temperature, the nitinol configured to assume a deployed configuration shape above the transition temperature thereof to anchor in tissue, such that a force exerted by the nitinol causes deployment of the first securing mechanism after withdrawal of the sheath.

18. The method of claim 13 wherein the step of inserting the implantable lead is performed by:
  making a first incision and a second incision;
  making a first tunnel between the first and second incisions;
  making a second tunnel from the second incision to an end location; and
  passing at least the second end of the implantable lead through the second incision to the end location, wherein the step of inserting the implantable lead is performed such that the retention device is accessible near the second incision, and the method further comprises positioning the retention device near a xiphoid of the patient and partly withdrawing the sheath allowing the one or more securing mechanisms to extend to the deployed configuration and push against tissue of the patient near the second incision to secure the lead in a selected position.

* * * * *